(12) United States Patent
Dannaher

(10) Patent No.: US 9,220,508 B2
(45) Date of Patent: Dec. 29, 2015

(54) SURGICAL CLIP APPLIER WITH ARTICULATION SECTION

(71) Applicant: Ethicon Endo-Surgery, Inc., Cincinnati, OH (US)

(72) Inventor: William D. Dannaher, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 243 days.

(21) Appl. No.: 14/020,131

(22) Filed: Sep. 6, 2013

(65) Prior Publication Data

US 2015/0073439 A1    Mar. 12, 2015

(51) Int. Cl.

| | | |
|---|---|---|
| *A61B 17/10* | (2006.01) | |
| *A61B 17/128* | (2006.01) | |
| *A61B 17/08* | (2006.01) | |
| *A61B 17/122* | (2006.01) | |
| *A61B 17/00* | (2006.01) | |
| *A61B 17/29* | (2006.01) | |

(52) U.S. Cl.
CPC .............. *A61B 17/1285* (2013.01); *A61B 17/10* (2013.01); *A61B 17/083* (2013.01); *A61B 17/122* (2013.01); *A61B 2017/00986* (2013.01); *A61B 2017/00991* (2013.01); *A61B 2017/2902* (2013.01); *A61B 2017/2908* (2013.01)

(58) Field of Classification Search
CPC .. A61B 17/10; A61B 17/122; A61B 17/1285; A61B 2017/00986; A61B 2017/2902; A61B 2017/2908; A61B 17/068
USPC .......................................... 606/139, 142, 143
See application file for complete search history.

(56) References Cited

U.S. PATENT DOCUMENTS

| | | |
|---|---|---|
| 5,163,945 A | 11/1992 | Ortiz et al. |
| 5,342,373 A | 8/1994 | Stefanchik et al. |
| 5,415,334 A | 5/1995 | Williamson, IV et al. |
| 5,431,668 A | 7/1995 | Burbank, III et al. |
| 5,445,167 A | 8/1995 | Yoon et al. |

(Continued)

FOREIGN PATENT DOCUMENTS

| | | |
|---|---|---|
| EP | 1 749 479 | 2/2007 |
| WO | WO 95/29641 | 11/1995 |
| WO | WO 2012/006306 | 1/2012 |

OTHER PUBLICATIONS

International Search Report and Written Opinion dated Jan. 21, 2015 for Application No. PCT/US2014/052091.

*Primary Examiner* — Katherine M Shi
(74) *Attorney, Agent, or Firm* — Frost Brown Todd LLC

(57) ABSTRACT

An instrument for clamping a surgical clip has a handle assembly, a shaft assembly, and an end effector. The handle assembly has a trigger and an articulation knob. The shaft assembly has an outer ground tube, a middle articulation tube, and a push/pull tube disposed within the middle articulation tube. The trigger is operable to cause longitudinal translation of the push/pull tube. The outer ground tube and the middle articulation tube present mating angled faces sloped in opposing directions. Rotation of the articulation knob causes rotation of the middle articulation tube. Rotation of the middle articulation tube changes the orientation of the angled faces and thus causes articulation of the middle articulation tube and the push/pull tube. The end effector has a pair of jaws configured to apply a surgical clip to a vessel. Longitudinal translation of the push/pull tube causes closure of the pair of jaws.

20 Claims, 24 Drawing Sheets

(56) References Cited

U.S. PATENT DOCUMENTS

| | | |
|---|---|---|
| 5,465,895 A | 11/1995 | Knodel et al. |
| 5,575,799 A * | 11/1996 | Bolanos et al. .............. 606/139 |
| 5,597,107 A | 1/1997 | Knodel et al. |
| 5,601,573 A | 2/1997 | Fogelberg et al. |
| 5,632,432 A | 5/1997 | Schulze et al. |
| 5,673,840 A | 10/1997 | Schulze et al. |
| 5,951,574 A | 9/1999 | Stefanchik et al. |
| 6,500,176 B1 | 12/2002 | Truckai et al. |
| 6,783,524 B2 | 8/2004 | Anderson et al. |
| 6,796,203 B2 | 9/2004 | Dubrowskij |
| 6,978,921 B2 | 12/2005 | Shelton, IV et al. |
| 7,000,818 B2 | 2/2006 | Shelton, IV et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,261,724 B2 | 8/2007 | Molitor et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,404,508 B2 | 7/2008 | Smith et al. |
| 7,686,820 B2 | 3/2010 | Huitema et al. |
| 7,699,860 B2 | 4/2010 | Huitema et al. |
| 7,731,724 B2 | 6/2010 | Huitema et al. |
| 8,038,686 B2 | 10/2011 | Huitema et al. |
| 8,262,679 B2 | 9/2012 | Nguyen |
| 8,461,744 B2 | 6/2013 | Wiener et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0015660 A1 | 1/2011 | Wiener et al. |
| 2011/0087218 A1 | 4/2011 | Boudreaux et al. |

* cited by examiner

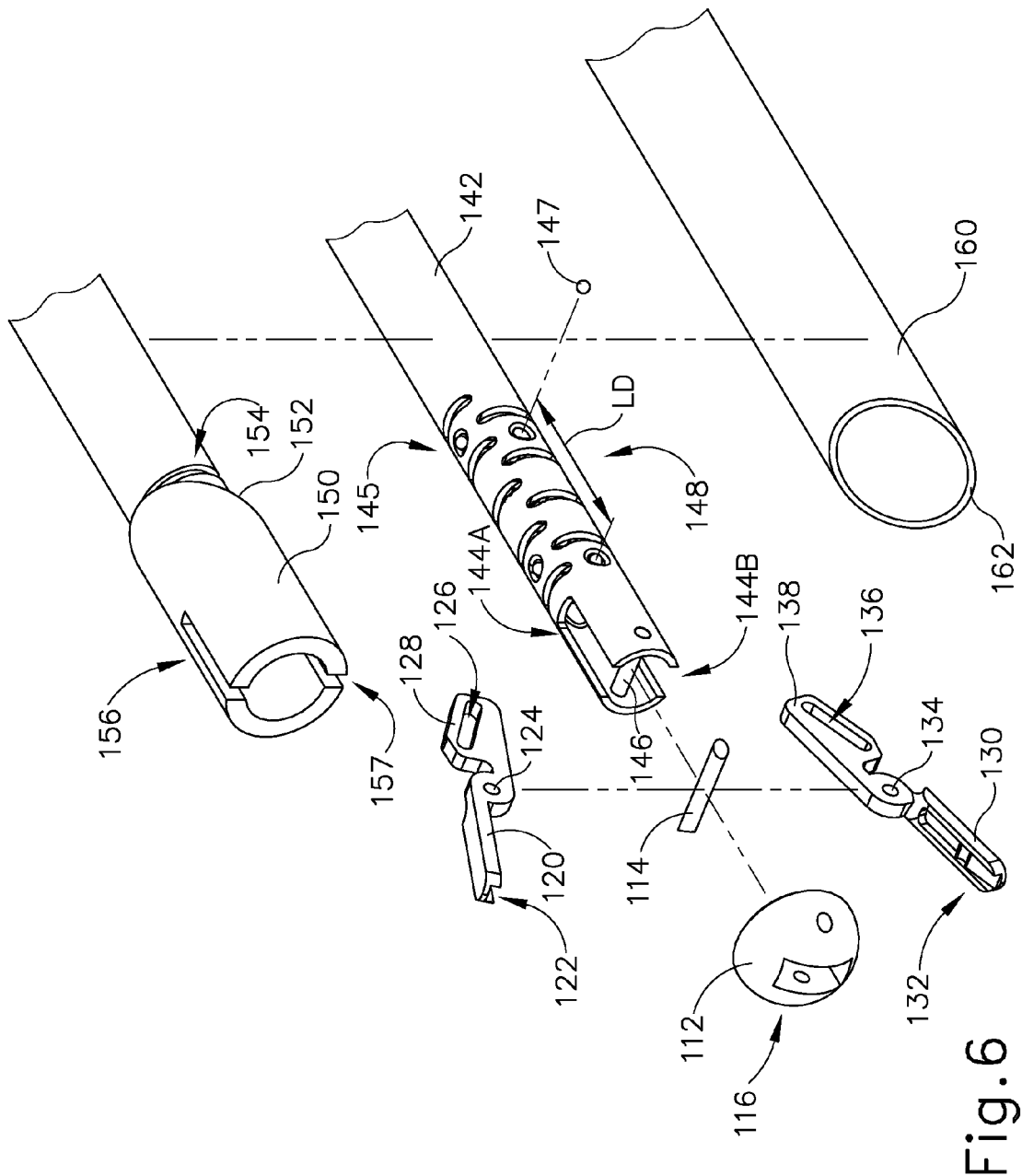

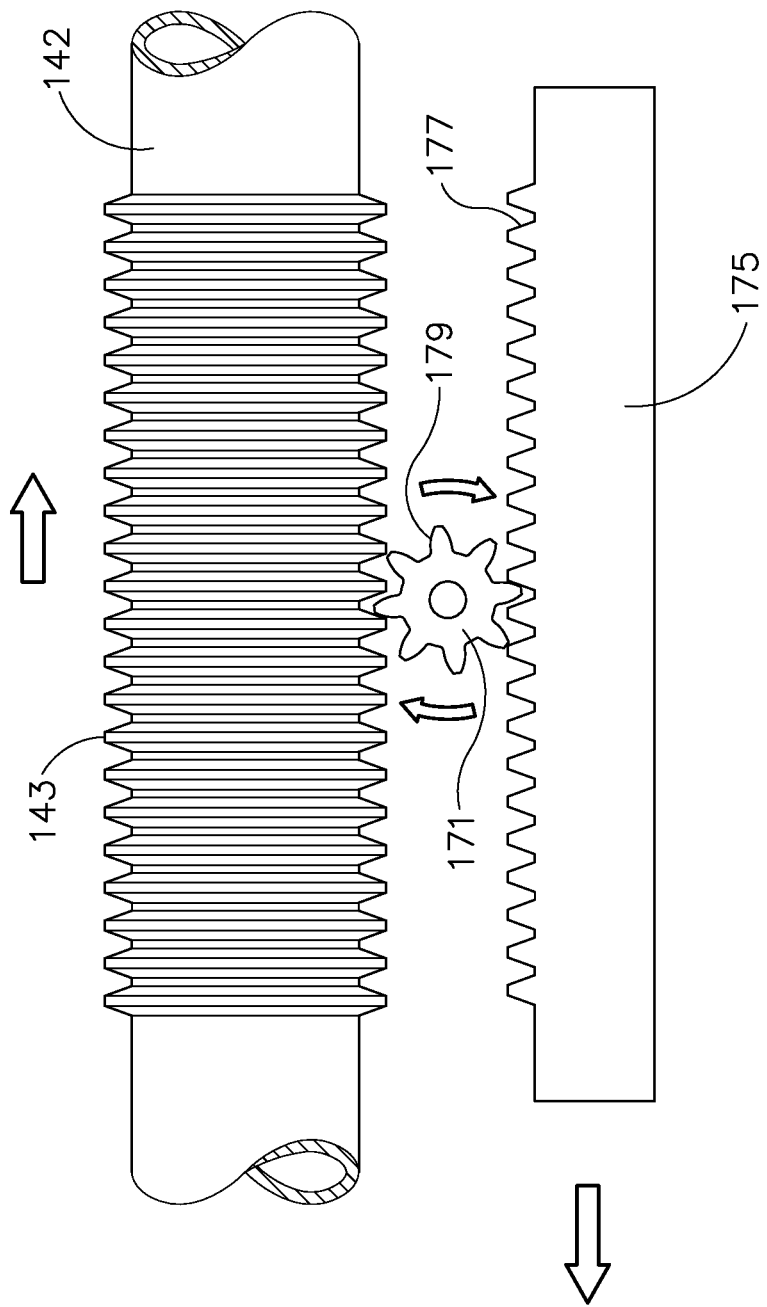

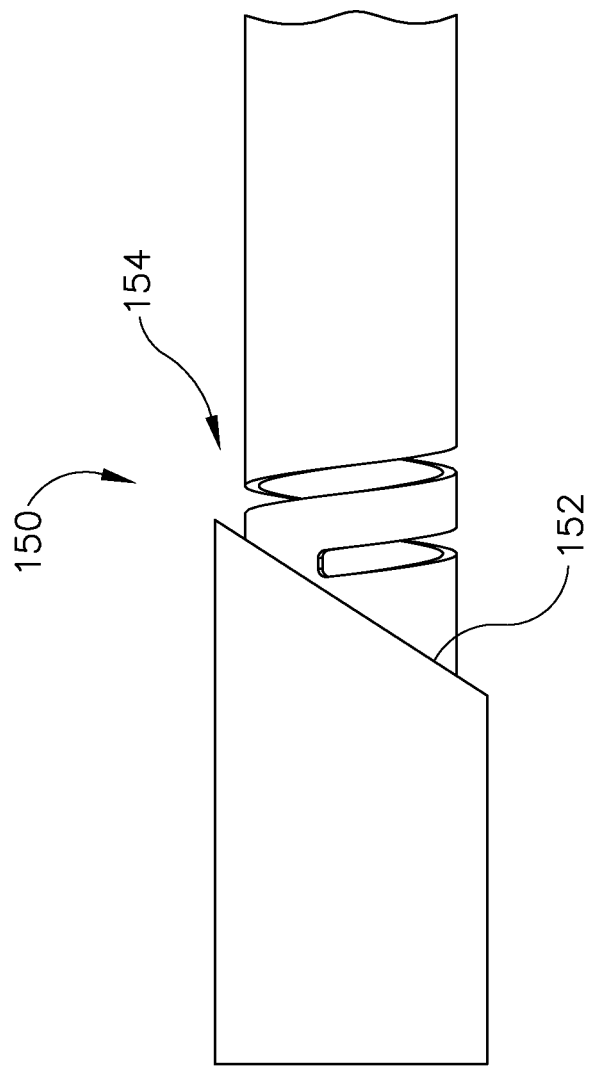

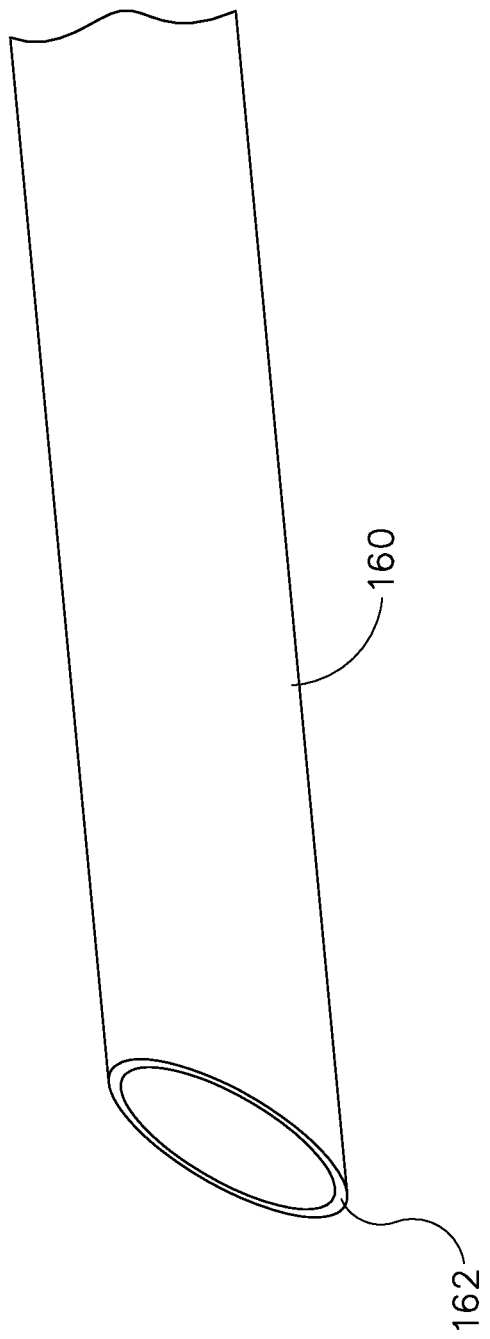

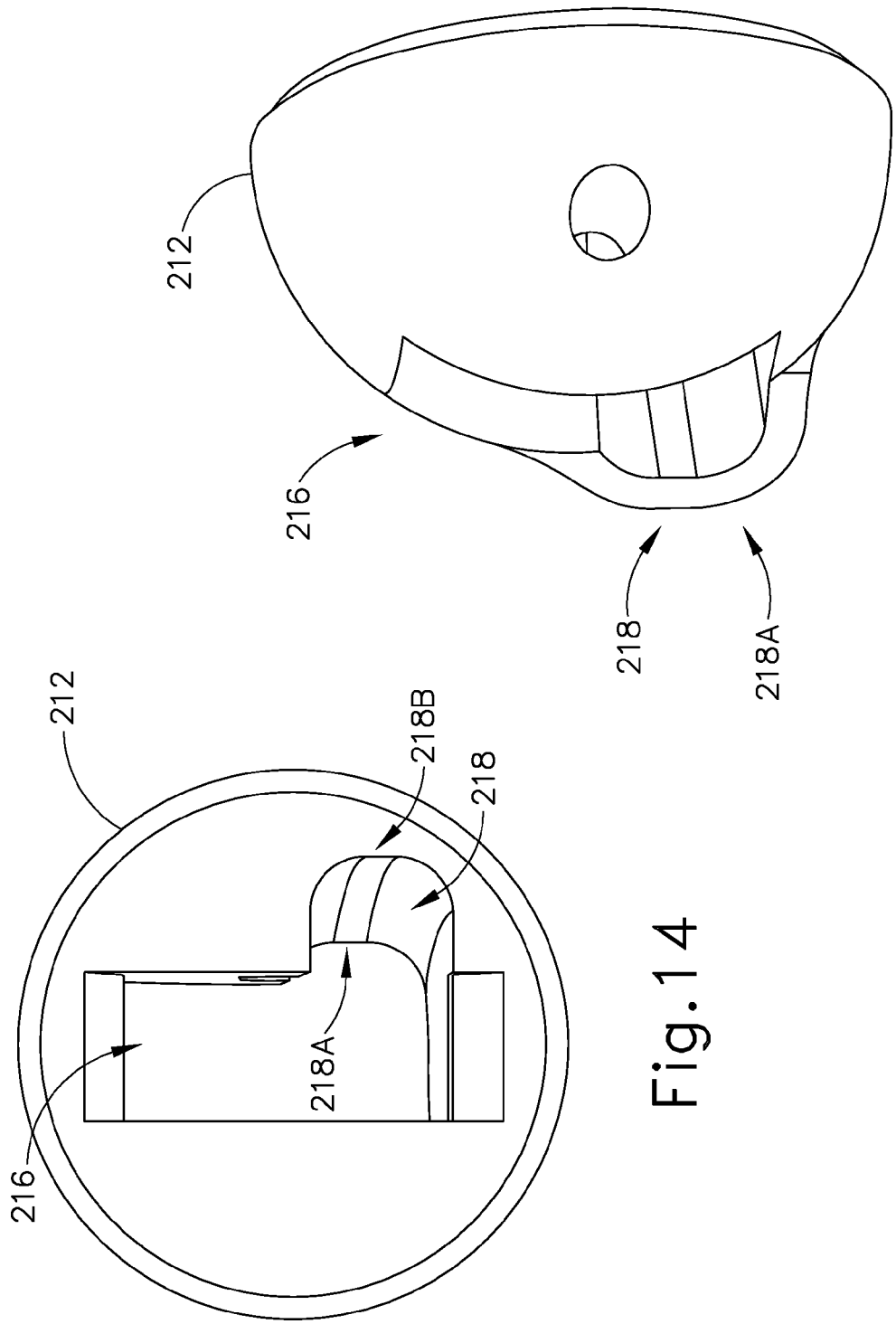

Fig.17B

SURGICAL CLIP APPLIER WITH ARTICULATION SECTION

BACKGROUND

Endoscopic surgical clip appliers may be used for a number of surgical procedures. In endoscopic or laparoscopic surgical procedures, access to the surgical site may be achieved through a trocar inserted through a small entrance incision in the skin. The trocar port allows the surgeon to insert a number of different surgical instruments therethrough and to perform surgical procedures within the patient in a minimally invasive manner.

During some surgical procedures, the surgeon may wish to terminate the flow of blood or another fluid through one or more vessels. In some such instances, the surgeon may apply a surgical clip to a blood vessel or another duct to prevent the flow of blood or other bodily fluids therethrough during the procedure. An endoscopic surgical clip applier is capable of applying a singular surgical clip or multiple surgical clips during a minimally invasive entry to the body cavity. For instance, an endoscopic surgical clip applier is capable of ligating a blood vessel by clamping a surgical clip about the blood vessel to thereby prevent blood flow through the vessel. Such clips may be fabricated from a malleable biocompatible material and may be compressed over a vessel. Alternatively, such clips may be fabricated from a resilient biocompatible material and may be released to resiliently clamp the vessel.

In some instances, application of clips may be complicated by a reduced field of view, reduced tactile feedback for the user at the proximal end of the device, and/or reduced access to the target vessel due to anatomical positioning or obstructions, etc. It may therefore be desirable to provide an ability to manipulate the position and orientation of the distal end of the surgical clip applier at the surgical site. This may include articulating the end effector of the surgical clip applier by deflecting the end effector away from a longitudinal axis defined by a shaft assembly of the surgical clip applier.

One example of a surgical clip applier is the LIGAMAX™ 5 by Ethicon Endo-Surgery, Inc. of Cincinnati, Ohio. Other examples of surgical clip appliers are represented by the LIGACLIP® series of surgical clip appliers by Ethicon Endo-Surgery, Inc. of Cincinnati, Ohio. Examples of surgical clips are represented by the LIGACLIP® series of surgical clips by Ethicon Endo-Surgery, Inc. of Cincinnati, Ohio. Still further examples of surgical clip appliers and surgical clips are disclosed in U.S. Pat. No. 5,163,945, entitled "Surgical Clip Applier," issued Nov. 17, 1992, the disclosure of which is incorporated by reference herein; U.S. Pat. No. 5,342,373, entitled "Sterile Clips and Instrument for their Placement," issued Aug. 30, 1994, the disclosure of which is incorporated by reference herein; U.S. Pat. No. 5,431,668, entitled "Ligating Clip Applier," issued Jul. 11, 1995, the disclosure of which is incorporated by reference herein; U.S. Pat. No. 5,445,167, entitled "Methods of Applying Surgical Clips and Suture Tie Devices to Bodily Tissue During Endoscopic Procedures," issued Aug. 29, 1995, the disclosure of which is incorporated by reference herein; U.S. Pat. No. 5,601,573, entitled "Sterile Occlusion Fasteners and Instruments and Methods for Their Placement," issued Feb. 11, 1997, the disclosure of which is incorporated by reference herein; U.S. Pat. No. 5,951,574, entitled "Multiple Clip Applier Having a Split Feeding Mechanism," issued Sep. 14, 1999, the disclosure of which is incorporated by reference herein; U.S. Pat. No. 7,261,724, entitled "Surgical Clip Advancement Mechanism," issued Aug. 28, 2007, the disclosure of which is incorporated by reference herein; U.S. Pat. No. 7,686,820, entitled "Surgical Clip Applier Ratchet Mechanism," issued Mar. 30, 2010, the disclosure of which is incorporated by reference herein; U.S. Pat. No. 7,699,860, entitled "Surgical Clip," issued Apr. 20, 2010, the disclosure of which is incorporated by reference herein; U.S. Pat. No. 7,731,724, entitled "Surgical Clip Advancement and Alignment Mechanism," issued Jun. 8, 2010, the disclosure of which is incorporated by reference herein; U.S. Pat. No. 8,038,686, entitled "Clip Applier Configured to Prevent Clip Fallout," issued Oct. 18, 2011, the disclosure of which is incorporated by reference herein; and U.S. Pat. No. 8,262,679, entitled "Clip Advancer," issued Sep. 11, 2012, the disclosure of which is incorporated by reference herein.

While various kinds of surgical clip appliers and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts an exploded perspective view of the end effector of FIG. 5 with an inner push/pull tube of the instrument of FIG. 1;

FIG. 7 depicts a top view of a trigger of the instrument of FIG. 1 in a rack and pinion relationship with the inner push/pull tube of FIG. 6;

FIG. 9 depicts a detailed side elevational view of the distal end of a middle articulation tube of the instrument of FIG. 1;

FIG. 10 depicts a detailed side elevational view of the distal end of an outer ground tube of the instrument of FIG. 1;

FIG. 14 depicts a rear elevational view of an exemplary cap that may be used with the instrument of FIG. 1;

FIG. 15 depicts a perspective view of the cap of FIG. 14;

FIG. 17B depicts a cross-sectional view of the cap of FIG. 14 disposed on the distal end of the end effector of FIG. 5, with the pair of jaws in a closed position about the first blood vessel, with the first surgical clip closed about the first blood vessel by the pair of jaws, and with the plurality of staples disposed in the end effector;

Figure 1:
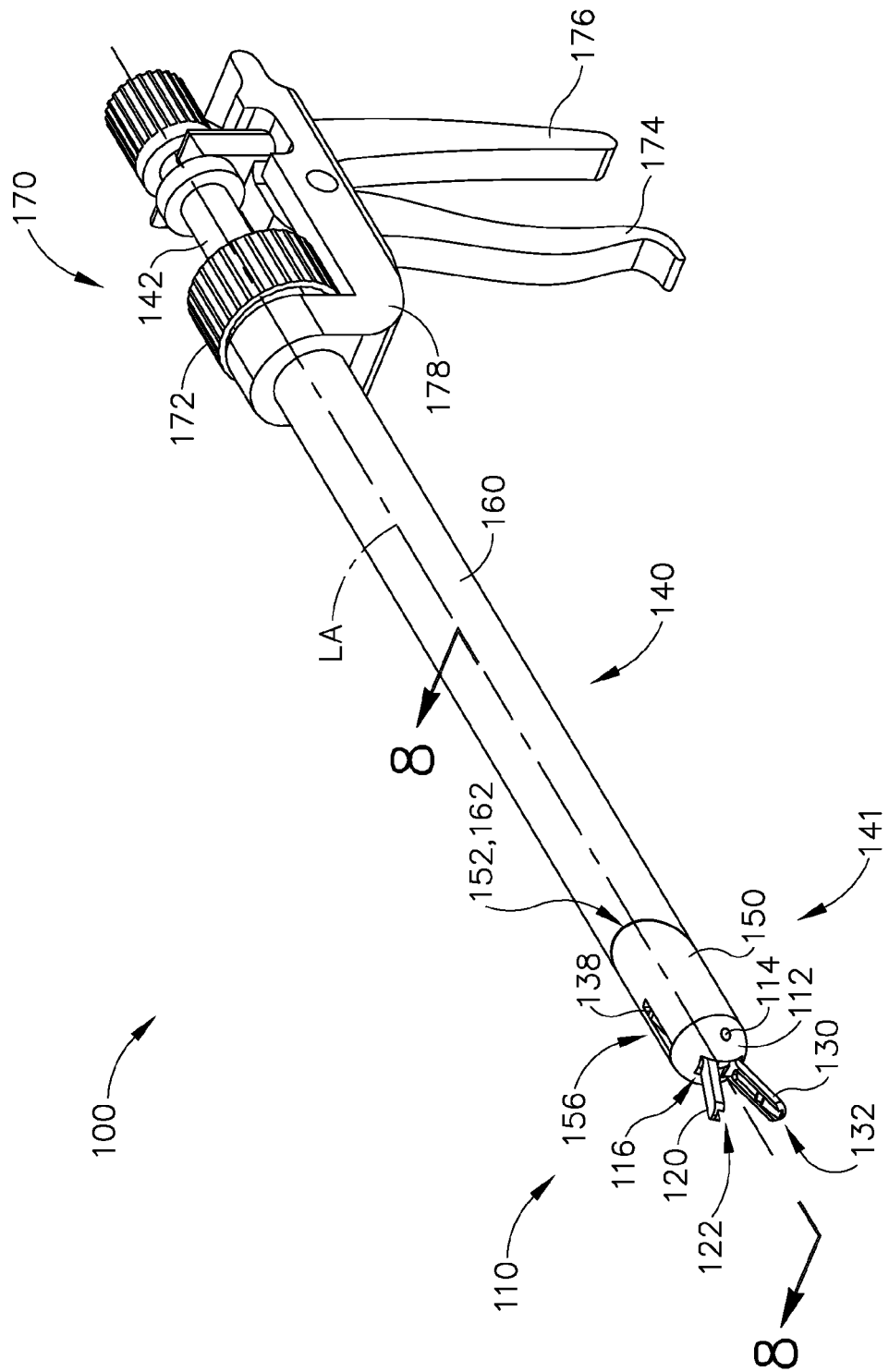
FIG. 1 depicts a perspective view of an exemplary clip applier instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Endoscopic Surgical Clip Applier

Figure 2:
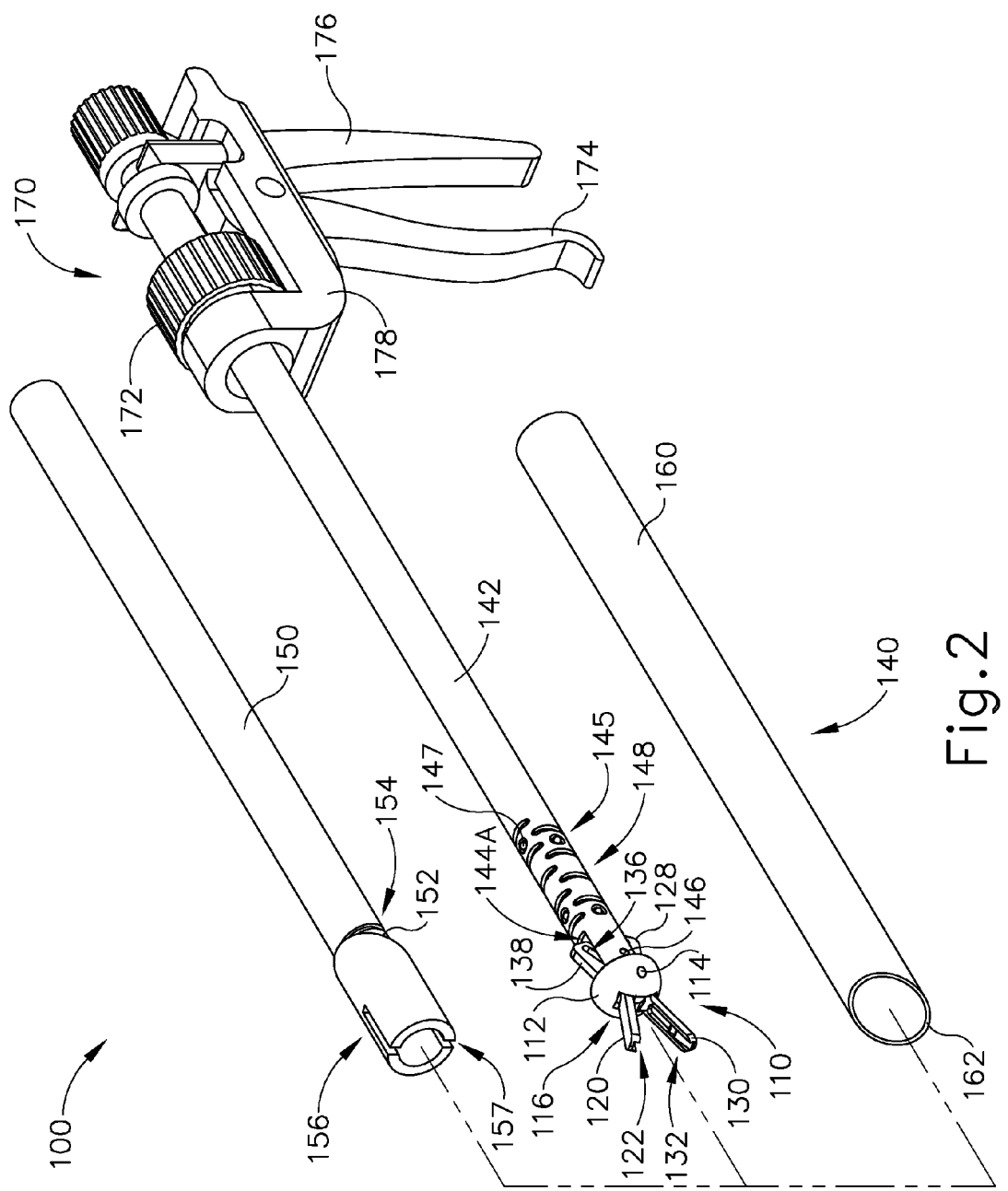
FIG. 2 depicts an exploded perspective view of the instrument of FIG. 1.

FIGS. 1-2 depict an exemplary surgical clip applier instrument (100) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (100) is used without a trocar. For instance, instrument (100) may be inserted directly through a thoracotomy or other type of incision. As another merely illustrative example, instrument (100) may be used in an open surgical procedure. Instrument (100) of the present example comprises an end effector (110), a shaft assembly (140), and a handle assembly (170), each of which will be described in more detail below. It should be understood that terms such as "proximal" and "distal" are used herein with reference to a clinician gripping handle assembly (170) of instrument (100). Thus, end effector (110) is distal with respect to the more proximal handle assembly (170). It will be further appreciated that for convenience and clarity, spatial terms such as "vertical" and "horizontal" are used herein with respect to the drawings. However, surgical instruments are used in many orientations and positions, and these terms are not intended to be limiting and absolute. It should also be understood that the teachings herein relating to instrument (100) may be readily combined with the various teachings of the various clip applier related patent references that are cited herein. Various suitable ways in which the teachings herein may be combined with the teachings of the clip applier related patent references that are cited herein will be apparent to those of ordinary skill in the art.

Figure 11:
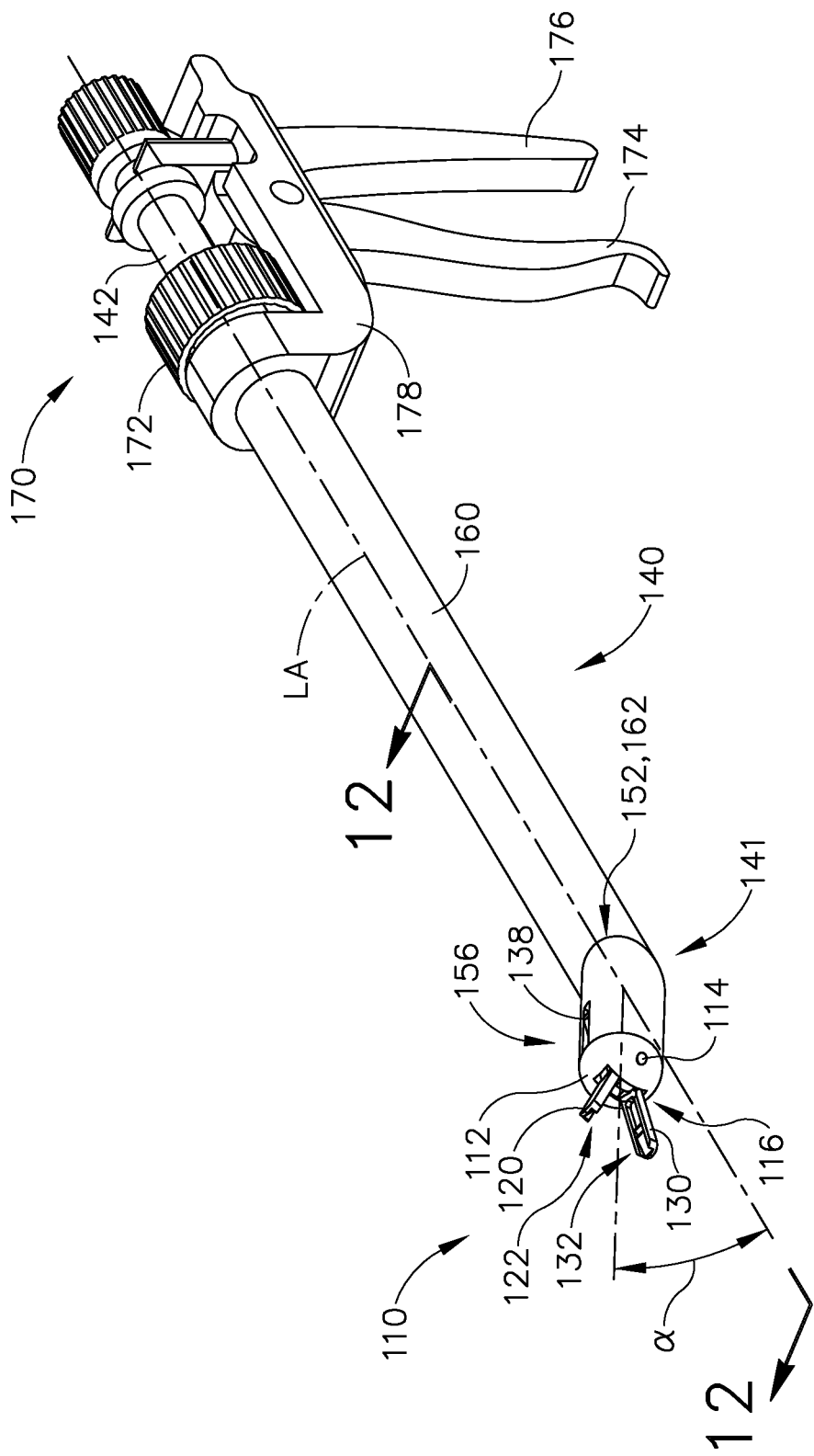
FIG. 11 depicts a perspective view of the instrument of FIG. 1 with the end effector of FIG. 3 in an articulated position.

Shaft assembly (140) extends distally from actuator handle assembly (170) and end effector (110) is coupled to a distal end of shaft assembly (140). Shaft assembly (140) comprises an articulation joint (141) proximal to end effector (110). Shaft assembly (140) and end effector (110) are inserted through a trocar while articulation joint (141) is in a non-articulated state. Once articulation joint (141) and end effector (110) have passed through the trocar and are positioned in the patient, articulation joint (141) may be articulated by articulation knob (172), such that end effector (110) may be deflected from the longitudinal axis (LA) of shaft assembly (140) at a desired angle (a) as depicted in FIG. 11. End effector (110) may thereby reach behind an organ or approach vessels from a desired angle, etc.

Figure 4:
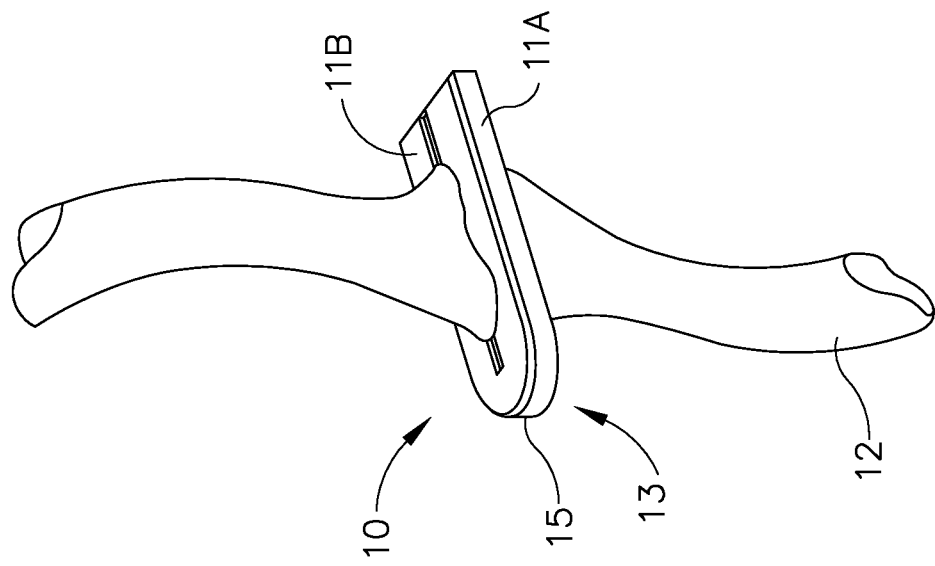
FIG. 4 depicts a perspective view of the surgical clip of FIG. 3 clamped about a blood vessel.
Figure 3:
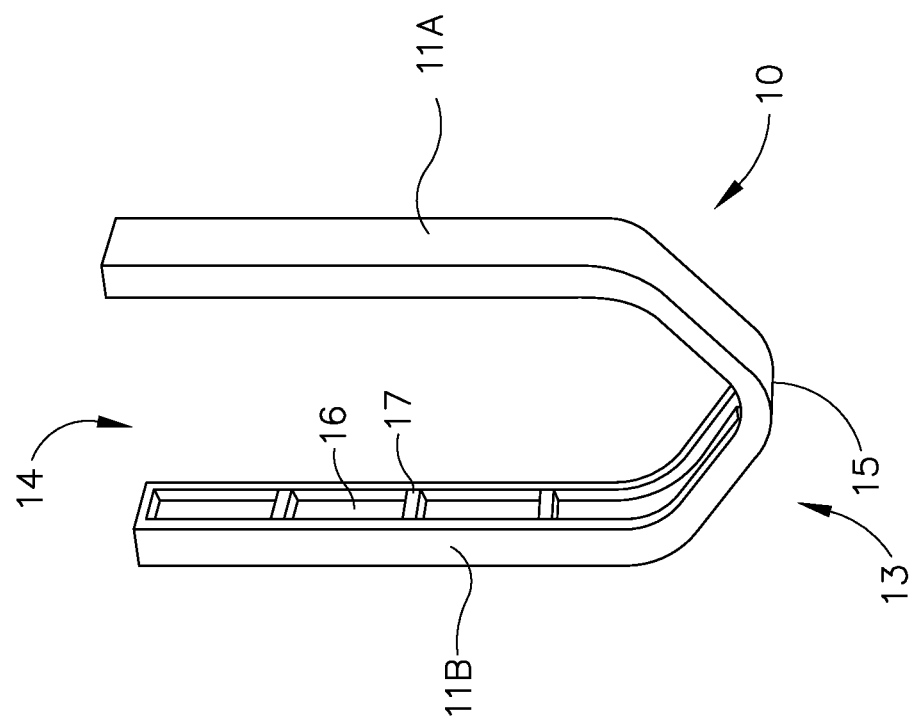
FIG. 3 depicts a perspective view of an exemplary surgical clip that may be used with the instrument of FIG. 1.

As shown in FIG. 3, clip (10) of the present example comprises a pair of legs (11A, 11B) that define a gap (14) sized to receive a vessel (12). As described in greater detail below, a trigger (174) of actuator handle assembly (170) is operable to actuate a push/pull tube (142) of shaft assembly (140) to drive a pair of jaws (120, 130) of end effector (120) into a closed position and thereby clamp clip (10) about a vessel (12) as shown in FIG. 4. Accordingly, s vessel (12) may be clamped by utilizing instrument (100) to deploy clip (10) such that fluid may not pass through the vessel (12). Body member (13) presents an apex (15) about which legs (11A, 11B) and the remainder of body member (13) pivot such that clip (10) may be tightly clamped. In the present example, a plurality of pockets (16) define a series of raised lips (17) within the interior surfaces of legs (11A, 11B) such that the force caused by the clamping of jaws (120, 130) becomes localized along raised lips (17). This may further promote the stoppage of blood flow. In addition or in the alternative, the tissue of vessel (12) may become trapped within pockets (16), further reducing any risk that clip (10) might inadvertently slide off of vessel (12). Alternatively, other kinds of features may be provided within the interior surfaces of legs (11A, 11B); or the interior surface of legs (11A, 11B) may simply be flat. Clip (10) may be formed of a malleable metal and/or various other suitable materials. It should also be understood that clip (10) is just one example; and that various other kinds of clips may be used in instrument (100). Various other suitable forms that clip (10) may take will be apparent to those of ordinary skill in the art in view of the teachings herein.

II. Exemplary Clip Applying Assembly

Figure 5:
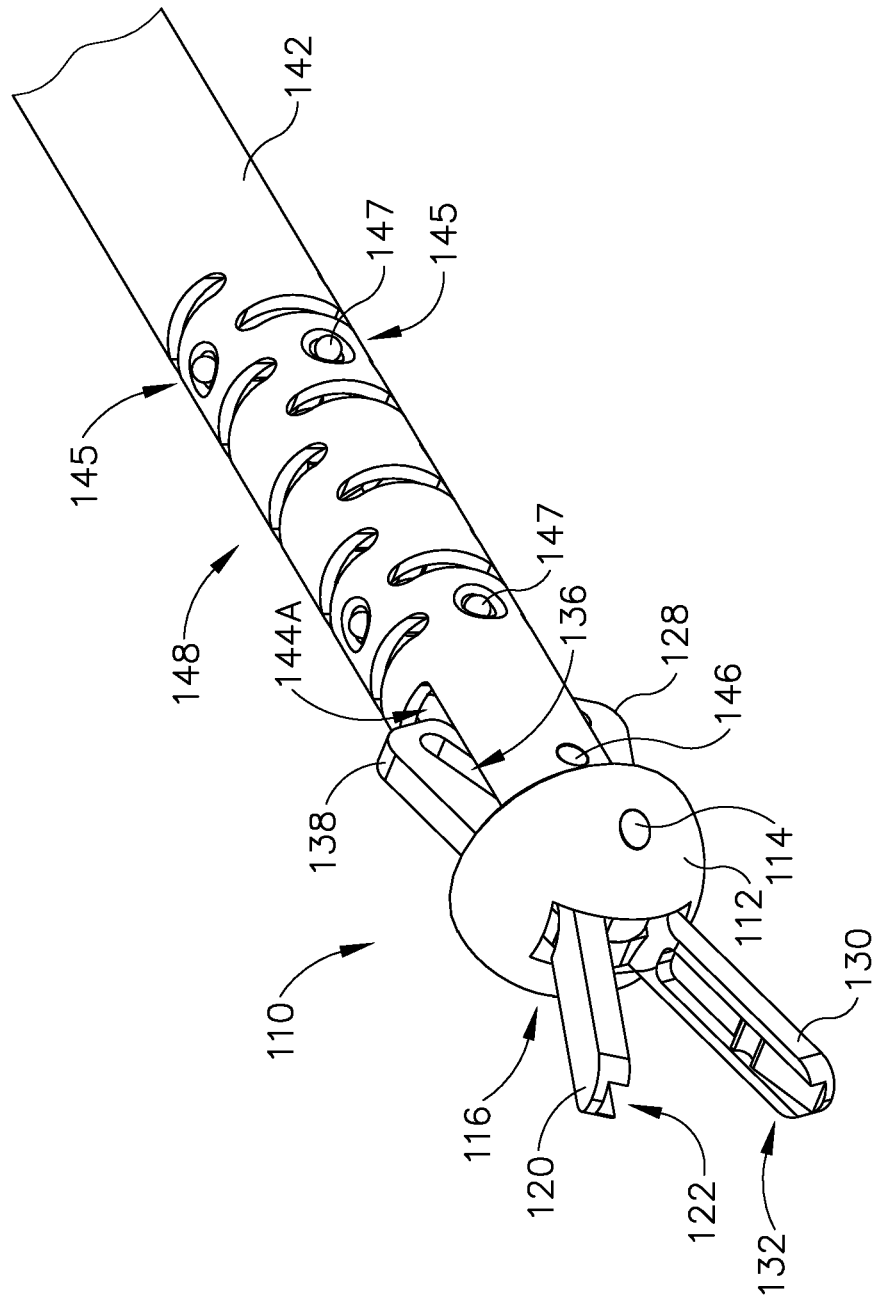
FIG. 5 depicts a detailed perspective view of the end effector of the instrument of FIG. 1.

As best seen in FIGS. 5-6, end effector (110) of the present example comprises a lower jaw (130), an upper jaw (120), a cap (112), and a pivot pin (114). Jaws (120, 130) are pivotable about pivot pin (114) toward and away from one another to drive clamping of clip (10). A distal portion of lower jaw (130) presents a lower channel (132) that is configured to receive and temporarily secure a first portion of clip (10). A distal portion of upper jaw (120) presents an upper channel (122) that is configured to receive and temporarily secure a second portion of clip (10). Upper channel (122) and lower channel (132) are oriented such that channels (122, 132) open such that clip (10) may be inserted into and temporarily secured within jaws (120, 130) when jaws (120, 130) are in an open position. Channels (122, 132) may further comprise features to promote releasable engagement between clip (10) and jaws (120, 130). A proximal portion (138) of lower jaw (130) presents a slot (136). A proximal portion (128) of upper jaw (120) also presents a slot (126). Slots (126, 136) are positioned adjacent to each other such that portions of slots (126, 136) are aligned with each other during operation of instrument (100).

As shown in FIGS. 5-6, cap (112) is rigidly coupled to a distal end of a middle articulation tube (150). Cap (112) has a round shape to prevent snagging or tearing as instrument (100) is inserted or positioned within a patient. Pivot pin (114) is disposed within and secured to cap (112) such that a portion of pivot pin (114) passes through a slot (116) of cap (112). The outer ends of pivot pin (114) are shaped to match the rounded contour of cap (112) such that the outer ends of pivot pin (114) are flush with cap (112). Jaws (122, 124) are disposed within slot (116). Jaws (120, 130) each define a respective opening (124, 134). Pivot pin (114) is rotatably disposed within openings (124, 134) within slot (116) such that jaws (120, 130) rotate about pivot pin (114) within slot (116). Jaws (120, 130) pivot about a point—openings (124, 134)—between channels (122, 132) at the distal portions of jaws (120, 130) and slots (126, 136) at the proximal portions (128, 138) of jaws (120, 130). Slot (116) is sizably configured to allow jaws (120, 130) to freely pivot about pivot pin (114). Jaws (120, 130) are operable to pivotally transition between an open position (FIG. 8A) to receive clip (10) and a closed position (FIG. 8B) to clamp clip (10) about vessel (12) as shown in FIG. 4.

Figure 8A:
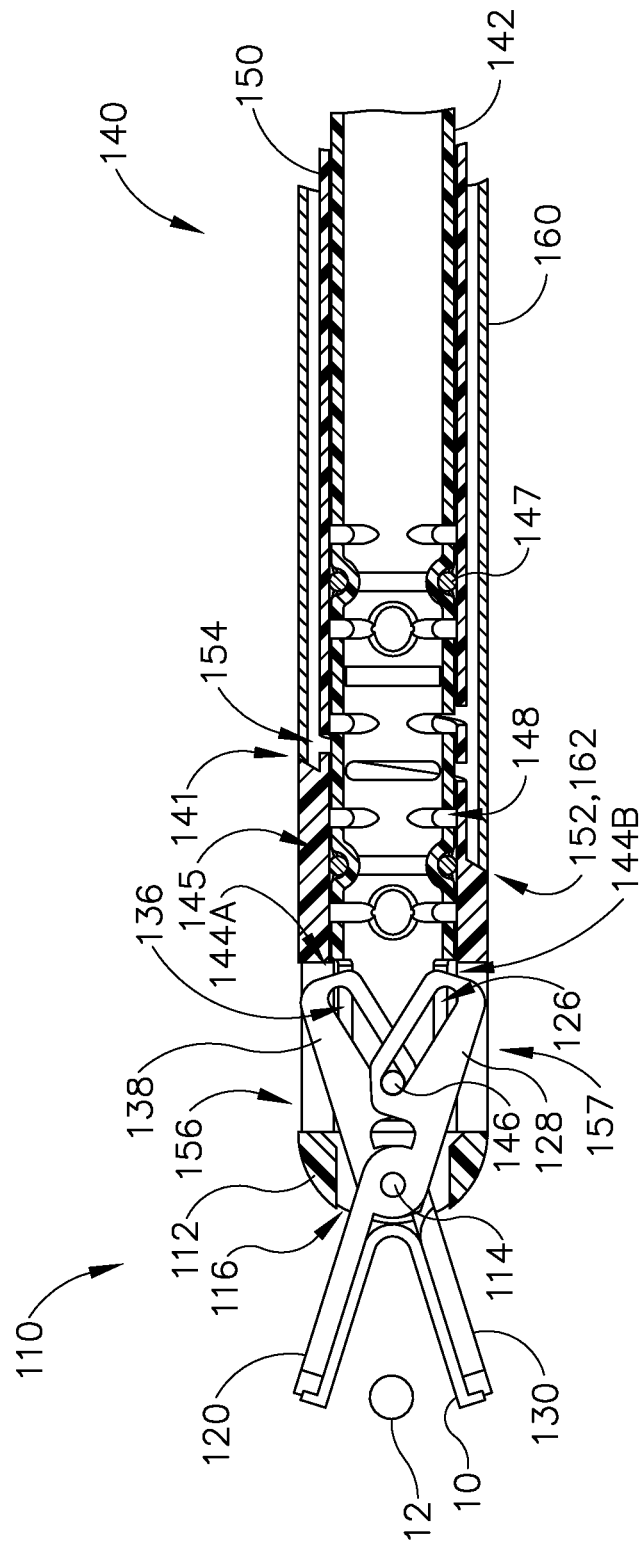
FIG. 8A depicts a cross-sectional view of the end effector of FIG. 5, taken along line 8-8 of FIG. 1, with a pair of jaws in an open position about a blood vessel.
Figure 8B:
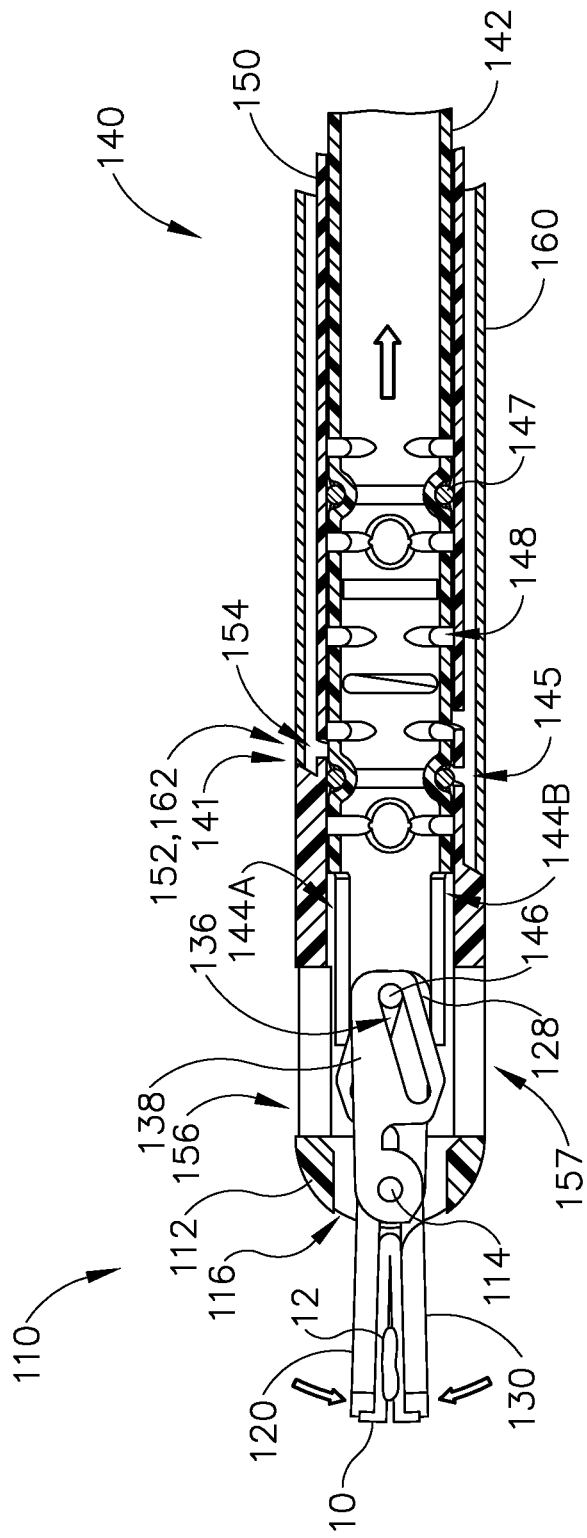
FIG. 8B depicts a cross-sectional view of the end effector of FIG. 5, taken along line 8-8 of FIG. 1, with the pair of jaws in a closed position about the blood vessel.

Shaft assembly (140) of the present example comprises a push/pull tube (142), middle articulation tube (150), and an outer ground tube (160). As will be discussed in more detail below, push/pull tube (142) is longitudinally translatable with respect to handle assembly (170) to cause clamping, or closing, of jaws (120, 130) of end effector (110). End effector (110) is disposed at a distal end of middle articulation tube (150). Middle articulation tube (150) defines a pair of slots (156A, 156B). Proximal portions (128, 138) of jaws (120, 130) are freely disposed within longitudinal slots (156A, 156B) when jaws (120, 130) are in an open position. Push/pull tube (142) is coaxially slidably disposed within middle articulation tube (150). A distal end of push/pull tube (142) defines a pair of longitudinal slots (144A, 144B) substantially aligned with longitudinal slots (156A, 156B). As best seen in FIG. 5, proximal portions (128, 138) of jaws (120, 130) are freely disposed within longitudinal slots (144A, 144B) when jaws (120, 130) are in an open position. A drive pin (146) is disposed within and secured to the distal end of push/pull tube (142) transverse to longitudinal slots (144A, 144B) and transverse to the longitudinal axis of push/pull tube (142). Drive pin (146) is slidably and rotatably disposed within slots (126, 136) of jaws (120, 130). As best seen in FIGS. 8A-8B, distal ends of slots (126, 136) overlap, and drive pin (146) is disposed within this overlapping region, when jaws (120, 130) are in an open position. As will be discussed in more detail below, longitudinal translation of push/pull tube (142) and drive pin (146) causes jaws (120, 130) to pivot about pivot pin (114). In particular, proximal longitudinal translation of drive pin (146) within slots (126, 136) will drive jaws (120, 130) toward each other into a closed position.

As shown in FIGS. 1-2, handle assembly (170) includes a body (178), a pistol grip (176), trigger (174), and articulation knob (172). Trigger (174) is pivotable toward and away from pistol grip (176) to cause clamping, or closing, of jaws (122, 124) of end effector (120). Such closing of jaws (122, 124) is provided through push/pull tube (142), which longitudinally translates relative to handle assembly (170) and relative to shaft assembly (140) in response to pivoting of trigger (174) relative to pistol grip (176). For instance, as shown in FIG. 7, trigger (174) and push/pull tube (142) may have a rack and pinion relationship such that distal motion of upper end (175) of trigger (174) will cause proximal motion of push/pull tube (142). In particular, upper end (175) of trigger (174) is laterally offset from push/pull tube (142) and presents a plurality of teeth (177). Push/pull tube (142) comprises a plurality of annular teeth (143) longitudinally disposed along an exterior surface push/pull tube (142). A pinion gear (171) is rotatably disposed between upper end (175) of trigger (174) and push/pull tube (142). Pinion gear (171) presents a plurality of teeth (179) annularly disposed about pinion gear (171). Teeth (179) of pinion gear (171) engage teeth (177) of trigger (174) on a first side of pinion gear (171) and teeth (143) of push/pull tube (142) on an opposite second side of pinion gear (171). It should therefore be understood that distal motion of upper end (175) of trigger (174) would cause clockwise rotation of pinion gear (171). This clockwise rotation of pinion gear (171) would in turn cause proximal motion of push/pull tube (142). In some other versions, trigger (174) and push/pull tube (142) are coupled through a set of pivoting linkages. Various other suitable relationships between trigger (174) and push/pull tube (142) will be apparent to those of ordinary skill in the art in view of the teachings herein.

Push/pull tube (142) extends along the length of shaft assembly (140) and, as discussed above, is mechanically associated with jaws (120, 130) by way of slots (126, 136) and drive pin (146). Longitudinal translation of push/pull tube (142) and drive pin (146) causes jaws (120, 130) to pivot about pivot pin (114). As shown in FIG. 8A, when jaws (120, 130) are in an open position, distal ends of slots (126, 136) overlap, and drive pin (146) is disposed within this overlapping region. In this open position, proximal ends of slots (126, 136) are not overlapping. As push/pull tube (142) is translated longitudinally proximally, drive pin (146) translates proximally within slots (126, 136) and causes proximal ends of slots (126, 136) to overlap, thus pivoting jaws (120, 130) about pivot pin (114) into a closed position as shown in FIG. 8B. It should therefore be understood that pivoting of trigger (174) toward pistol grip (176) causes clamping, or closing, of jaws (120, 130) of end effector (110). This clamping, or closing, of jaws (120, 130) will cause clip (10) to close as well. When jaws (120, 130) are subsequently opened by advancing push/pull tube (142) distally, jaws (120, 130) will release clip (10) such that another clip may be received in jaws (120, 130). As shown in FIG. 8B, distal ends of slots (126, 136) are not overlapping when jaws (120, 130) are in the closed position. As push/pull tube (142) is translated longitudinally distally, drive pin (146) translates distally within slots (126, 136) and causes distal ends of slots (126, 136) to overlap once again, thus pivoting jaws (120, 130) about pivot pin (114) and thereby returning jaws (120, 130) into the open position as shown in FIG. 8A.

In some versions of instrument (100), jaws (120, 130) may be resiliently biased toward the open position. For instance, a torsion spring may be provided about pivot pin (114) to bias jaws (120, 130) toward the open position. It should be understood that this bias of jaws (120, 130) would bias push/pull tube (142) distally and also bias trigger (174) away from pistol grip (176). Alternatively, a compression spring may be provided to bias push/pull tube (142) distally, to thereby bias jaws (120, 130) toward the open position and further bias trigger (174) away from pistol grip (176). Alternatively, a torsion spring may be provided within handle assembly (170) to bias trigger (174) pivotably away from pistol grip (176) such that push/pull tube (142) is biased distally and jaws (120, 130) are biased toward the open position. It should therefore be understood that releasing trigger (174) away from pistol grip (176) may cause opening of jaws (122, 124) of end effector (110). Alternatively, some versions of instrument (100) may lack any bias that would cause the release of trigger (174) to open jaws (120, 130). In some such versions, a user must manually drive trigger (174) away from pistol grip (176) to open jaws (120, 130).

Although slots (126, 136) of the present example are shown as being straight, slots (126, 136) may instead be curved or have any other appropriate shape. It should be appreciated that curved slots may alter and/or cause a variable closing speed and/or closing force of jaws (120, 130) as jaws (120, 130) are closed.

In versions that enable reloading of clips (10) into jaws (120, 130) after deployment of a first clip (10), it should be understood that clips (10) may be reloaded into jaws (120, 130) in a number of ways, such as manually or mechanically via actuation of a reloading device disposed within instrument (100). In some versions, instrument (100) may be removed from the patient and each clip (10) may be loaded into jaws (120, 130) manually. As another variation, each clip (10) may be loaded into jaws (120, 130) manually while end effector (110) is still disposed in the patient. Alternatively, instrument (100) may be configured such that as jaws (120, 130) are pivoted from the closed position to the open position, clip (10) is automatically driven distally into jaws (120, 130). In some such versions, a series of clips (10) may be positioned in an end-to-end relationship along at least part of the length of shaft assembly (140).

For instance, FIGS. 14-17E show an exemplary alternative pair of jaws (220, 230) and an exemplary alternative cap (212) rigidly coupled to the distal end of middle articulation tube (150) in place of cap (112). Jaws (220, 230) are configured to operate substantially similar to jaws (120, 130) discussed above. For instance, jaws (220, 230) are pivotable about pivot pin (114) toward and away from one another to drive clamping of clip (10). As best seen in FIGS. 16A-16D, a distal portion of lower jaw (230) presents a lower channel (232) that is configured to receive and temporarily secure a first portion of clip (10). A proximal portion of lower channel (232) presents a transverse opening (234). A distal portion of upper jaw (220) presents an upper channel (222) that is configured to receive and temporarily secure a second portion of clip (10). Upper channel (222) and lower channel (232) are oriented such that channels (222, 232) open such that clip (10) may be inserted into and temporarily secured within jaws (220, 230) when jaws (220, 230) are in an open position. As best seen in FIGS. 14 and 15, cap (212) comprises a slot (216) configured to operate substantially similar to slot (116) of cap (112) as discussed above. Cap (212) further comprises a curved chute (218) defined in an interior surface of slot (216). Curved chute (218) presents a curved profile that transitions from a wide distal portion (218B) to a narrow proximal portion (218A). As best seen in FIG. 16A, curved chute (218) is oriented such that when jaws (220, 230) are in the open position, narrow proximal portion (218A) aligns with transverse opening (234) of lower jaw (230). In the present example, clips (10) are composed of a flexible, biocompatible thermoplastic, metal, or composite material such that, as shown in FIGS. 16A-16D and as will be discussed in more detail below, clips (10) may be driven through curved chute (218), transverse opening (234), and into channels (222, 232) of jaws (220. 230).

Figure 17A:
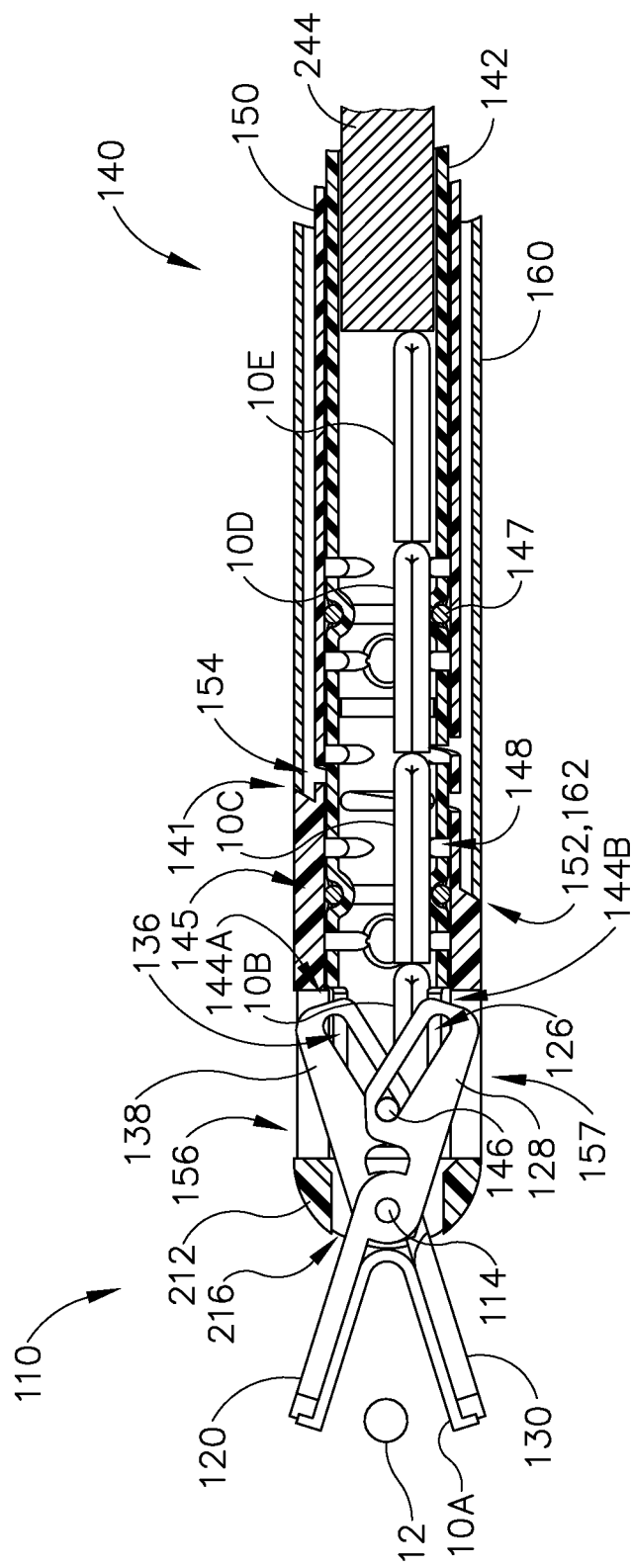
FIG. 17A depicts a cross-sectional view of the cap of FIG. 14 disposed on the distal end of the end effector of FIG. 5, with the pair of jaws in a open position about a first blood vessel, with a first surgical clip disposed within the pair of jaws, and with a plurality of staples disposed in the end effector.
Figure 17B:
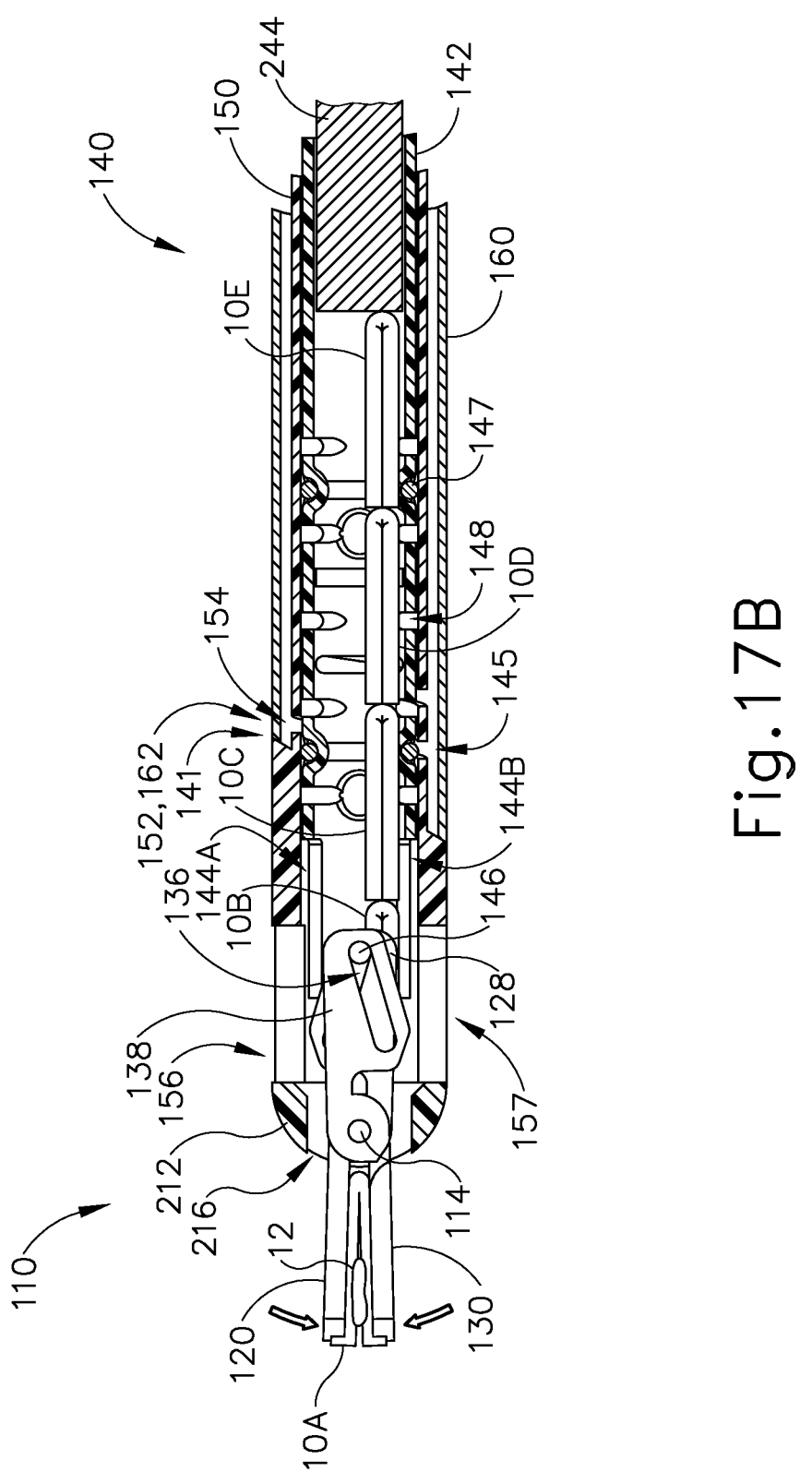
Figure 17C:
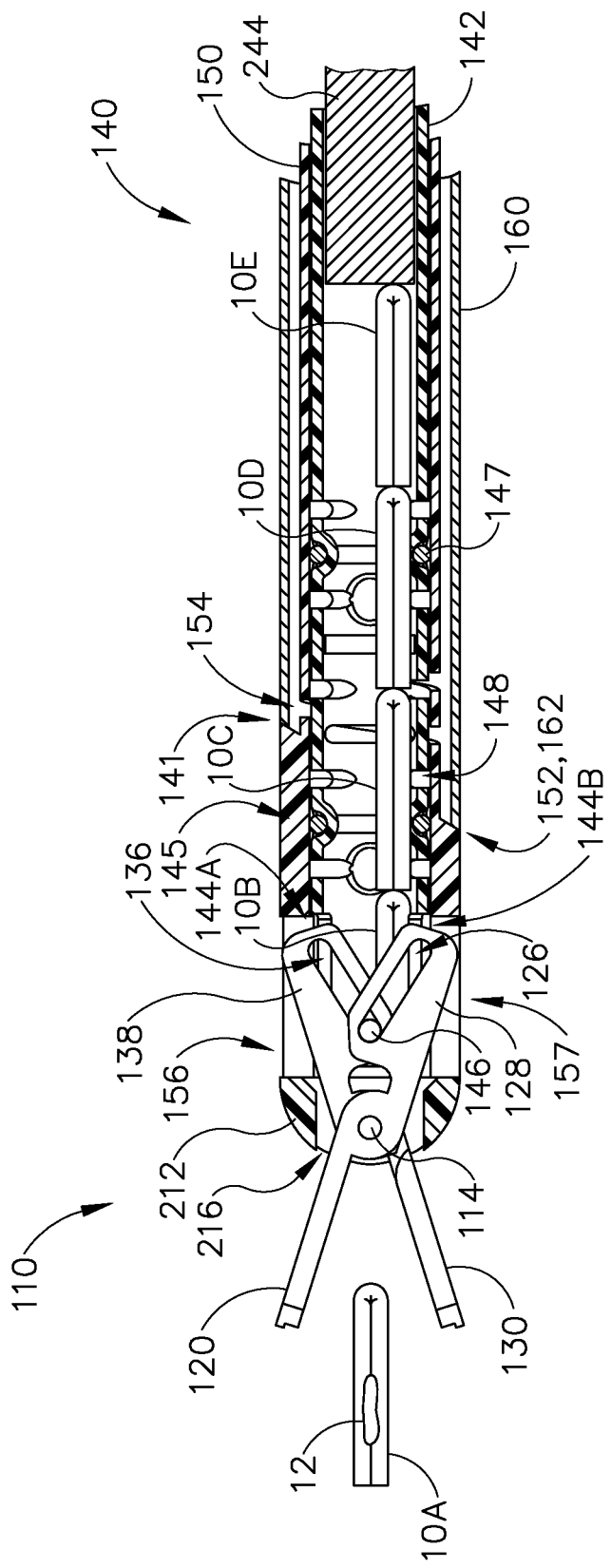
FIG. 17C depicts a cross-sectional view of the cap of FIG. 14 disposed on the distal end of the end effector of FIG. 5, with the pair of jaws in the open position, and with the plurality of staples disposed in the end effector.
Figure 17D:
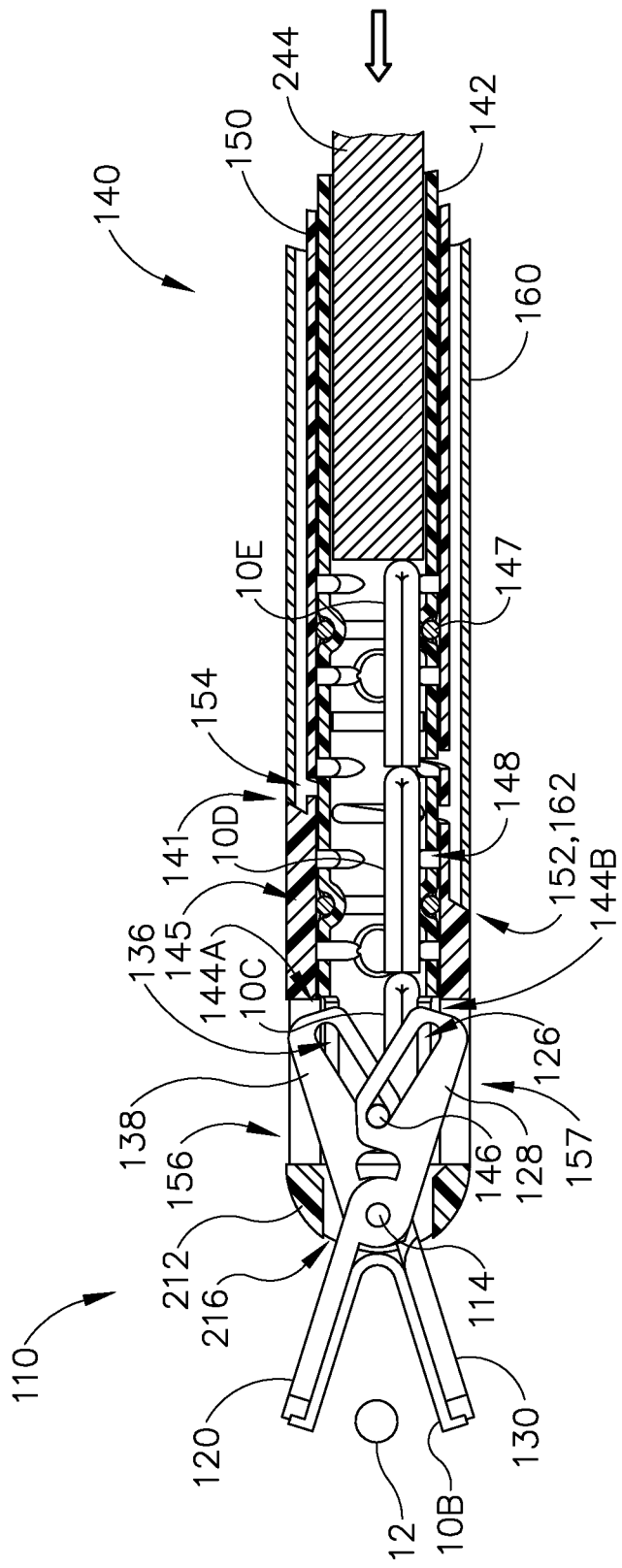
FIG. 17D depicts a cross-sectional view of the cap of FIG. 14 disposed on the distal end of the end effector of FIG. 5, with the pair of jaws in the open position about a second blood vessel, with a second surgical clip disposed within the pair of jaws, and with the plurality of staples disposed in the end effector.

As shown in FIG. 17A, with a first clip (10A) disposed within jaws (220, 230), a plurality of clips (10B, 10C, 10D, 10E) are disposed end-to-end within a distal end of push/pull tube (142). In this example, clips (10B, 10C, 10D, 10E) are sized, configured, and positioned such that clips (10B, 10C, 10D, 10E) are located between the longitudinal axis of push/pull tube (142) and the inner diameter surface of push/pull tube (142). A flexible rod (244) is disposed within push/pull tube (142) proximal to surgical clips (10B, 10C, 10D, 10E) and is configured to longitudinally drive clips (10B, 10C, 10D, 10E). A proximal end of flexible rod (244) extends proximally within push/pull tube (142) to handle assembly (170). Flexible rod (244) is configured to advance longitudinally distally within push/pull tube (142) to thereby drive clips (10B, 10C, 10D, 10E) distally. As will be apparent to those of ordinary skill in the art in view of the teachings herein, flexible rod (244) may be driven by a pivoting trigger, rotating knob, electromechanical motor, and or some other kind of driving feature that is positioned within handle assembly (170) or elsewhere. As shown in FIG. 17B, first clip (10A) is closed about vessel (12). As shown in FIG. 17C, first clip (10A) is then removed from jaws (220, 230) and remains closed about vessel (12) as jaws (220, 230) are moved back to the open position. Channels (222, 232) are then available to receive another surgical clip.

Figure 16A:
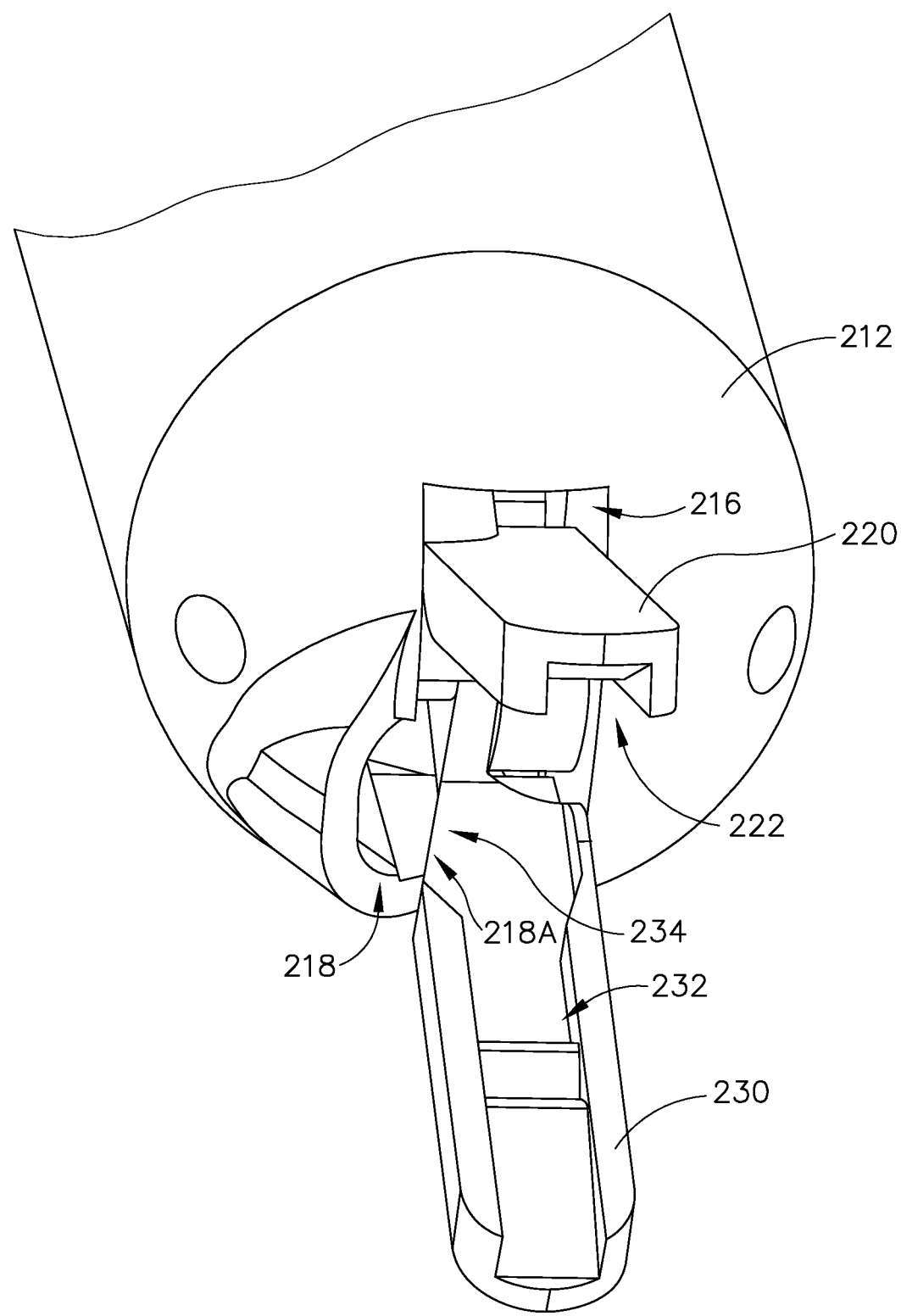
FIG. 16A depicts a perspective view of the cap of FIG. 14 disposed on a distal end of the end effector of FIG. 5 with an exemplary surgical clip in a first position.
Figure 16B:
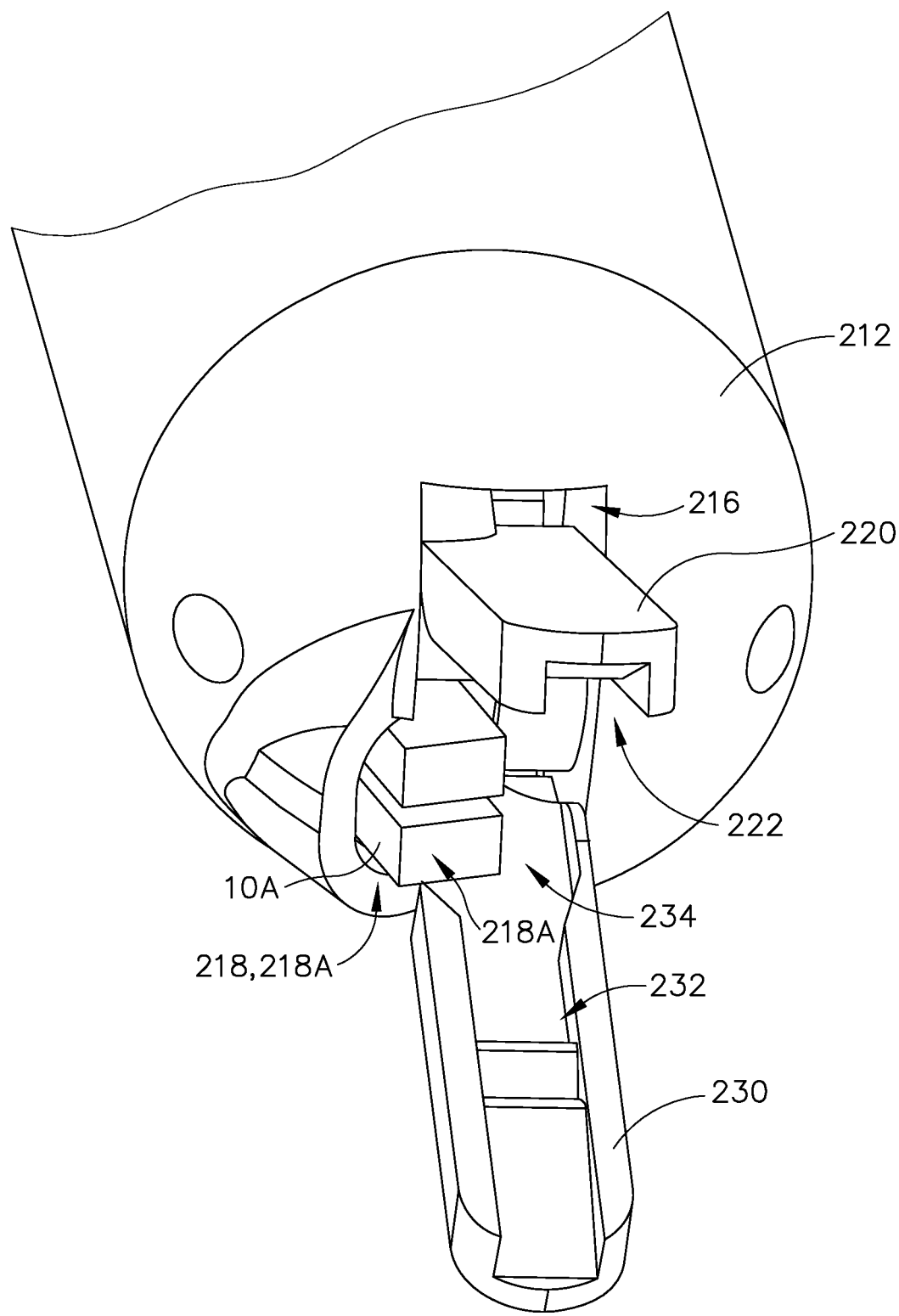
FIG. 16B depicts a perspective view of the cap of FIG. 14 disposed on the distal end of the end effector of FIG. 5 with the surgical clip in a second position.
Figure 16C:
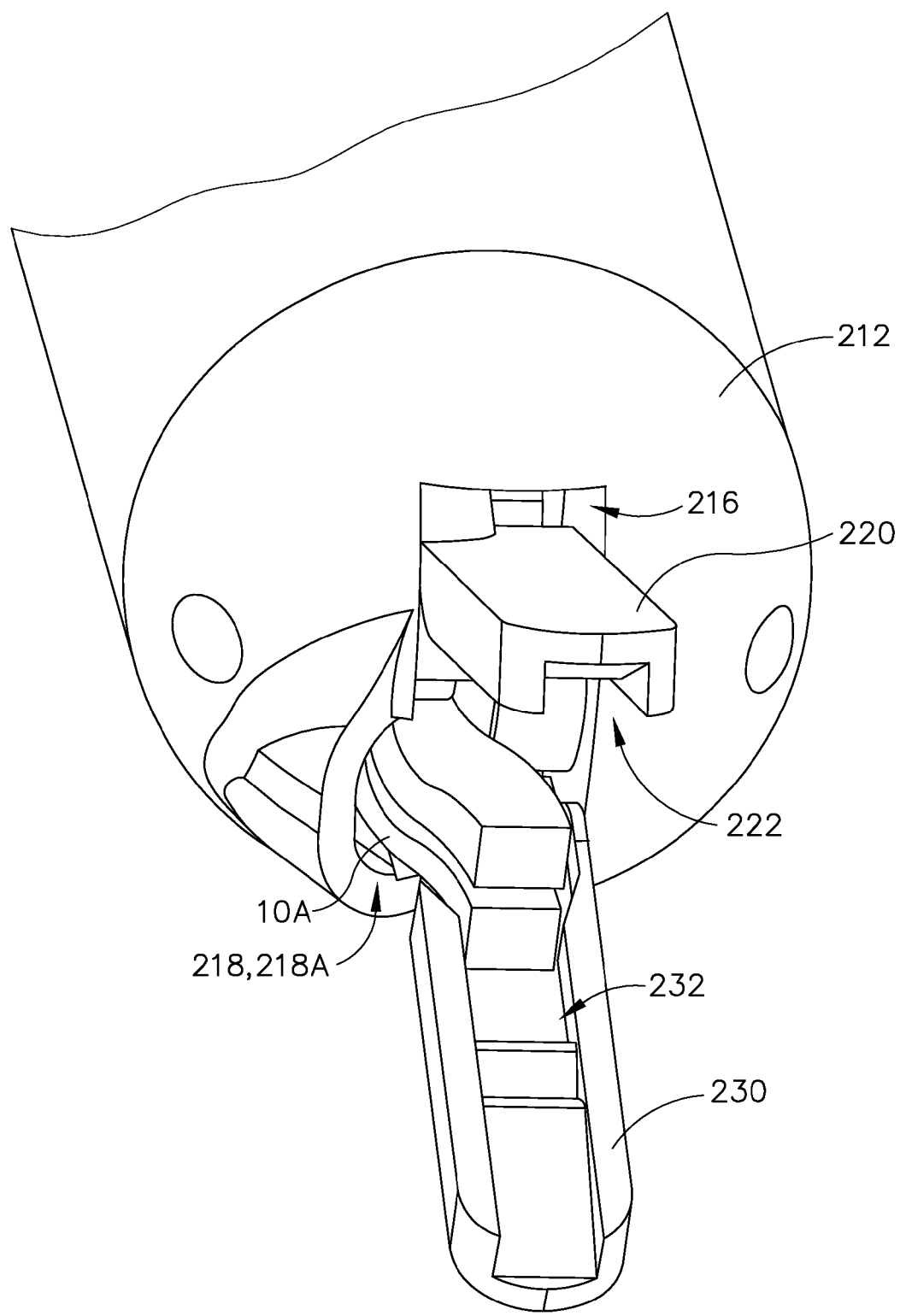
FIG. 16C depicts a perspective view of the cap of FIG. 14 disposed on the distal end of the end effector of FIG. 5 with the surgical clip in a third position.
Figure 16D:
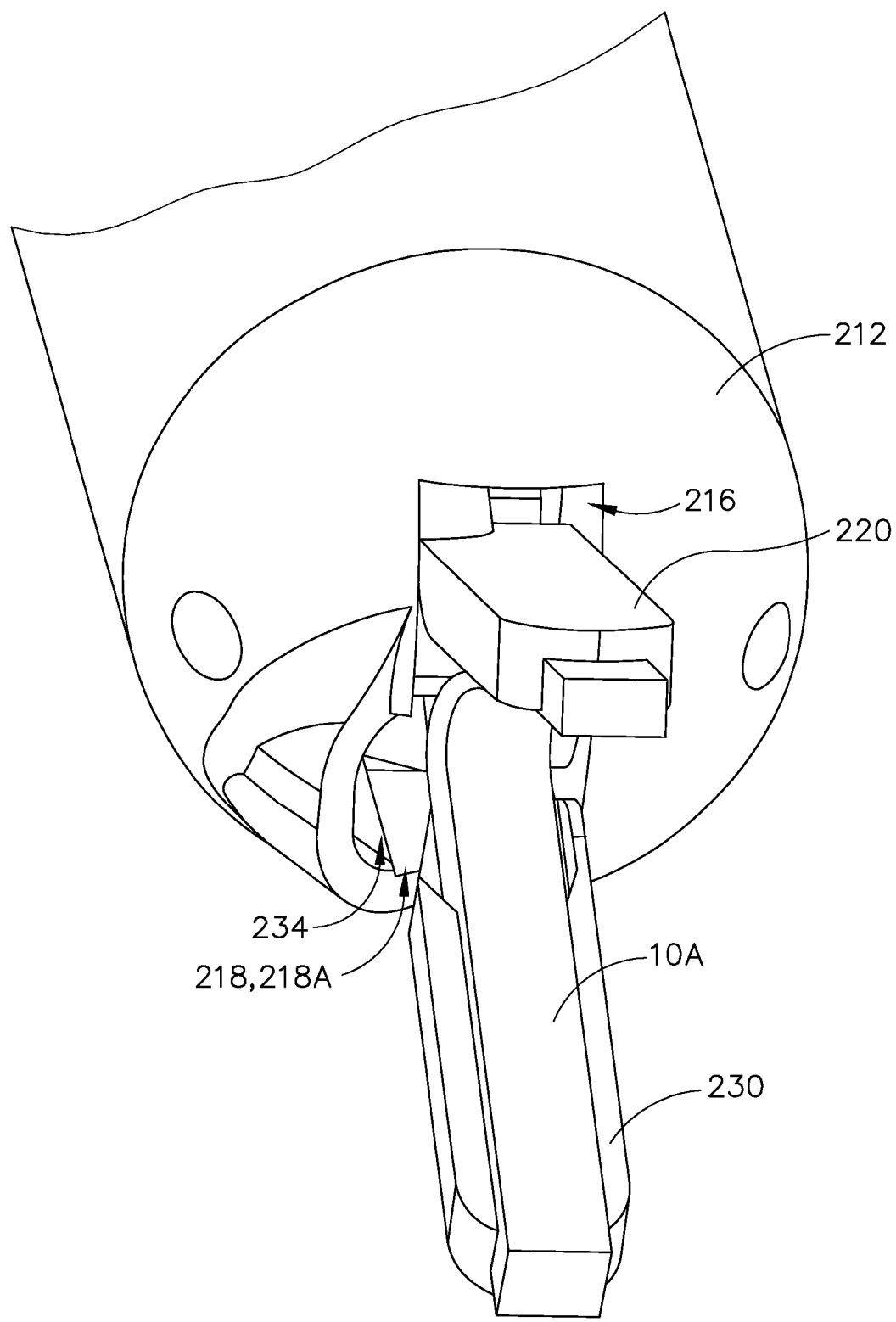
FIG. 16D depicts a perspective view of the cap of FIG. 14 disposed on the distal end of the end effector of FIG. 5 with the surgical clip in a fourth position.
Figure 17E:
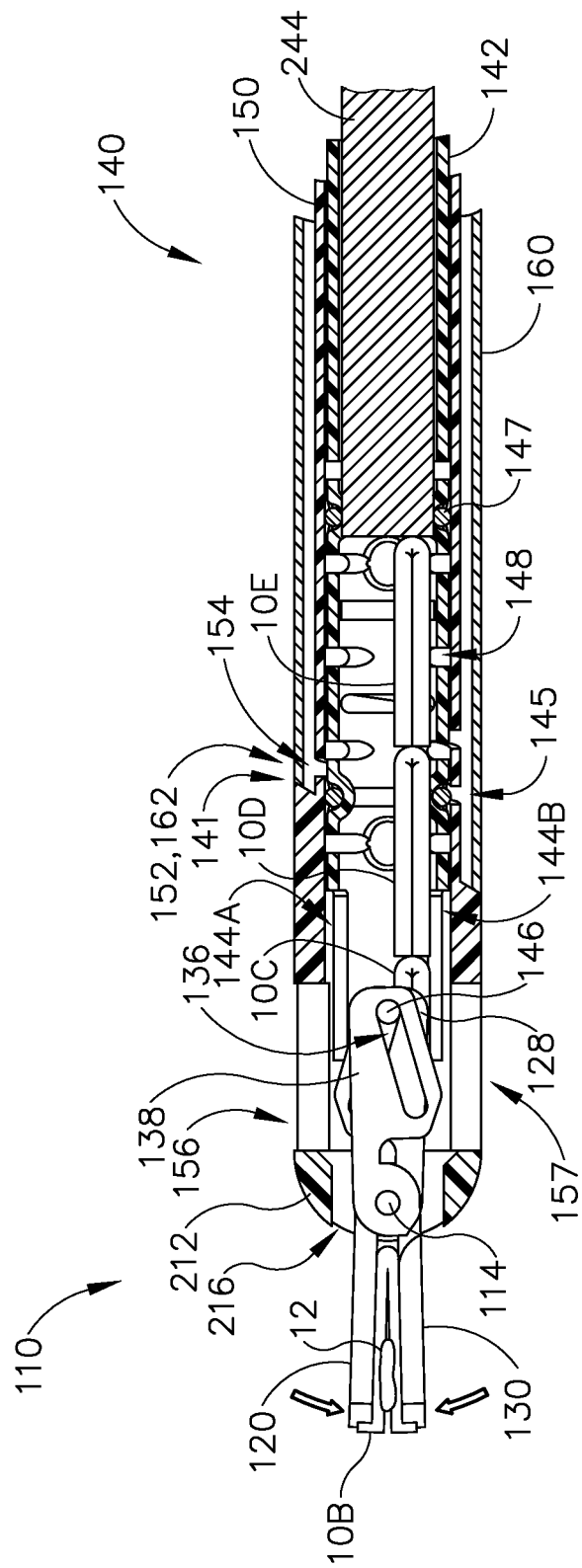
FIG. 17E depicts a cross-sectional view of the cap of FIG. 14 disposed on the distal end of the end effector of FIG. 5, with the pair of jaws in the closed position about the second blood vessel, with the second surgical clip closed about the second blood vessel by the pair of jaws, and with the plurality of staples disposed in the end effector.

As shown in FIGS. 17D and 16A-16D, flexible rod (244) is driven distally a distance equivalent to that of a single surgical clip such that a second clip (10B) is driven through curved chute (218) and transverse opening (234) (FIGS. 16B and 16C) and into channels (222, 232) of jaws (220, 230) (FIG. 16D). At this point, second clip (10B) may be closed about vessel (12) as shown in FIG. 17E. Clips (10A, 10B, 10C, 10D, 10E) may be resiliently biased such that after each clip (10A, 10B, 10C, 10D, 10E) is passed through curved chute (218), clips (10A, 10B, 10C, 10D, 10E) open to the position shown in FIG. 16D. It should be understood that push/pull tube (142) may comprise a plurality of inwardly directed projections, detents, channels, and/or other features that guide plurality of surgical clips (10A, 10B, 10C, 10D, 10E) through push/pull tube (142) and into curved chute (218) and cause clips (10A, 10B, 10C, 10D, 10E) to remain in a compressed configuration such that clips (10A, 10B, 10C, 10D, 10E) are able to pass under pins (114, 146). It should also be understood that in some versions of instrument (100) pins (114, 146) need not necessarily extend completely transversely through push/pull tube (142), such that clips (10A, 10B, 10C, 10D, 10E) may freely pass through push/pull tube (142).

Some versions of instrument (100) may be configured to deploy just a single clip (10), such that another clip (10) cannot be readily reloaded into jaws (120, 130). Such versions of instrument (100) may thus be simply replaced with a new pre-loaded instrument (100) in order to deploy a second clip (10). They may also slide the jaws over the clip manually to reload it one clip at a time.

III. Exemplary Articulation Assembly

As shown in FIGS. 5-6, a distal portion of push/pull tube (142) comprises a plurality of articulation slots (148) that are located proximal of longitudinal slots (144A, 144B) and are configured to provide flexibility at the distal end of push/pull tube (142). Articulation slots (148) are oriented transverse to longitudinal axis (LA). As best seen in FIG. 5, articulation slots (148) of the present example are disposed in pairs about the exterior of push/pull tube (142). Articulation slots (148) are angularly staggered along the length of the flexible region of push/pull tube (142). The distal portion of push/pull tube (142) further comprises a plurality of bearing detents (145) proximal of longitudinal slots (144A, 144B). Bearing detents (145) are configured to receive a plurality of ball bearings (147). Push/pull tube (142) is slidably disposed within middle articulation tube (150) in a coaxial relationship such that ball bearings (147) bear against an interior surface of middle articulation tube (150) as push/pull tube articulates and translates within middle articulation tube (150). Ball bearings (147) are configured to reduce friction between push/pull tube (142) and middle articulation tube (150), thereby reducing the force required to translate push/pull tube (142) within middle articulation tube (150), particularly when shaft assembly (140) is in an articulated state.

In some versions of instrument (100), ball bearings (147) may comprise a ferrous material. During assembly of some such versions of instrument (100), a magnetic rod (not shown) may be inserted into push/pull tube (142) as ball bearings (147) are loaded into bearing detents (145) to cause ball bearings (147) to remain in bearing detents (145). With the magnetic rod still inserted in push/pull tube (142), push/pull tube (142) may be inserted into middle articulation tube (150) thus trapping the ball bearings (147) between bearing detents (145) and the interior surface of middle articulation tube (150). After push/pull tube (142) has been suitably inserted into middle articulation tube (150), the magnetic rod may be removed from push/pull tube (142). Of course, various other assembly methods may be used.

As best seen in FIG. 9, middle articulation tube (150) presents a first sloped face (152). First sloped face (152) defines a first plane at a first angle that is oblique to longitudinal axis (LA) of shaft assembly (140). In the present example, the first angle is 45°, though it should be understood that any other suitable angle may be used. Middle articulation tube (150) comprises a helical articulation slot (154) that is located proximal of sloped face (152) and is configured to provide flexibility at the distal end of middle articulation tube (150). As best seen in FIG. 10, outer ground tube (160) presents a second sloped face (162). Second sloped face (162) is defines a second plane at a second angle oblique to longitudinal axis (LA) of shaft assembly (140). In the present example, the second angle is 45°, though it should be understood that any other suitable angle may be used. A proximal portion of middle articulation tube (150) is rotatably disposed within outer ground tube (160); while a distal portion of middle articulation tube (150) distal of first sloped face (152) remains exposed relative to outer ground tube (160). First sloped face (152) and second sloped face (162) are in contact with each other to form articulation joint (141), such that middle articulation tube (150) and outer ground tube (160) present a substantially flush exterior surface at first sloped face (152) and second sloped face (162). In the present example, first angle and second angle are complementary. Thus, as shown in FIG. 1, first sloped face (152) and second sloped face (162) align such that shaft assembly (140) is substantially straight in an unarticulated position. Articulation joint (141) is positioned such that sloped faces (152, 162) are located at the same longitudinal position as articulation slots (148) of push/pull tube (142).

Bearing detents (145) are positioned on opposite sides of helical articulation slot (154). Bearing detents (145) are further positioned such that a longitudinal distance (LD) between bearing detents (145) is greater than the distance of longitudinal translation of push/pull tube (142), in order to prevent ball bearings (147) from moving across and/or becoming lodged within helical articulation slot (154) when push/pull tube (142) is translated within middle articulation tube (150).

Articulation slots (148) and helical articulation slot (154) may be formed in push/pull tube (142) and middle articulation tube (150) by molding or machining (e.g., laser cutting, wire electrical discharge machining, milling, etc.) and/or using any other suitable techniques.

Although the first angle and the second angle of the present example are complementary by being equal and opposing, the first angle and the second angle need not necessarily be equal. For instance, the first angle may be 60° and the second angle may be 30°. Such values of the first and the second angle will allow first sloped face (152) and second sloped face (162) to align such that shaft assembly (140) is substantially straight in an unarticulated position. However, as will be appreciated from the discussion below, such values of the first angle and the second angle may change the degree of articulation of shaft assembly (140). It should also be understood that the first and second angles need not necessarily be complementary. For instance, the first angle may be 60° and the second angle may be 60°. Such values of the first angle and the second angle will allow first sloped face (152) and second sloped face (162) to align such that shaft assembly (140) always remains in an articulated position; while still permitting selective variation in the degree of articulation.

Figure 12A:
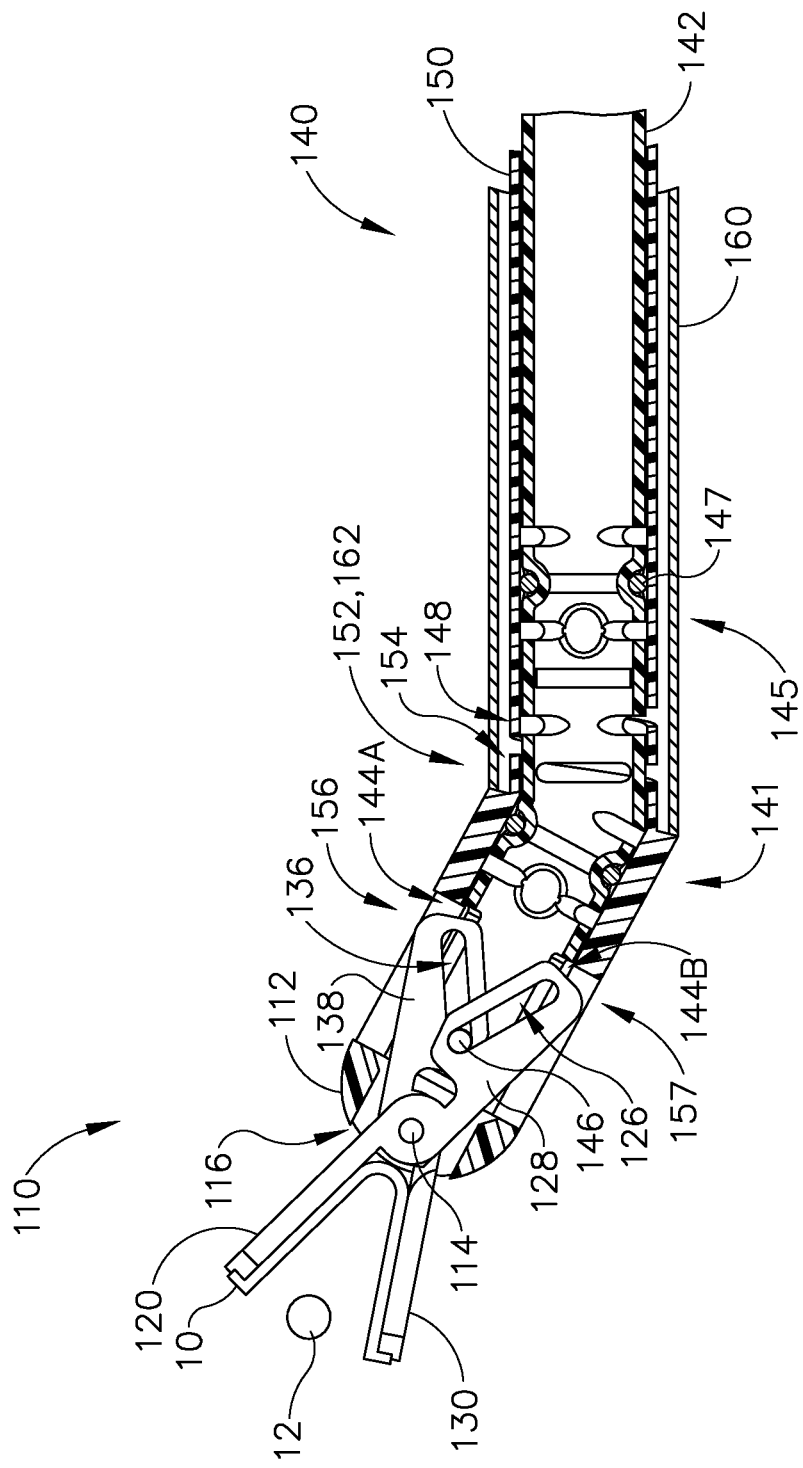
FIG. 12A depicts a cross-sectional view of the end effector of FIG. 5 in an articulated position, taken along line 12-12 of FIG. 11, with the pair of jaws in an open position about a blood vessel.
Figure 12B:
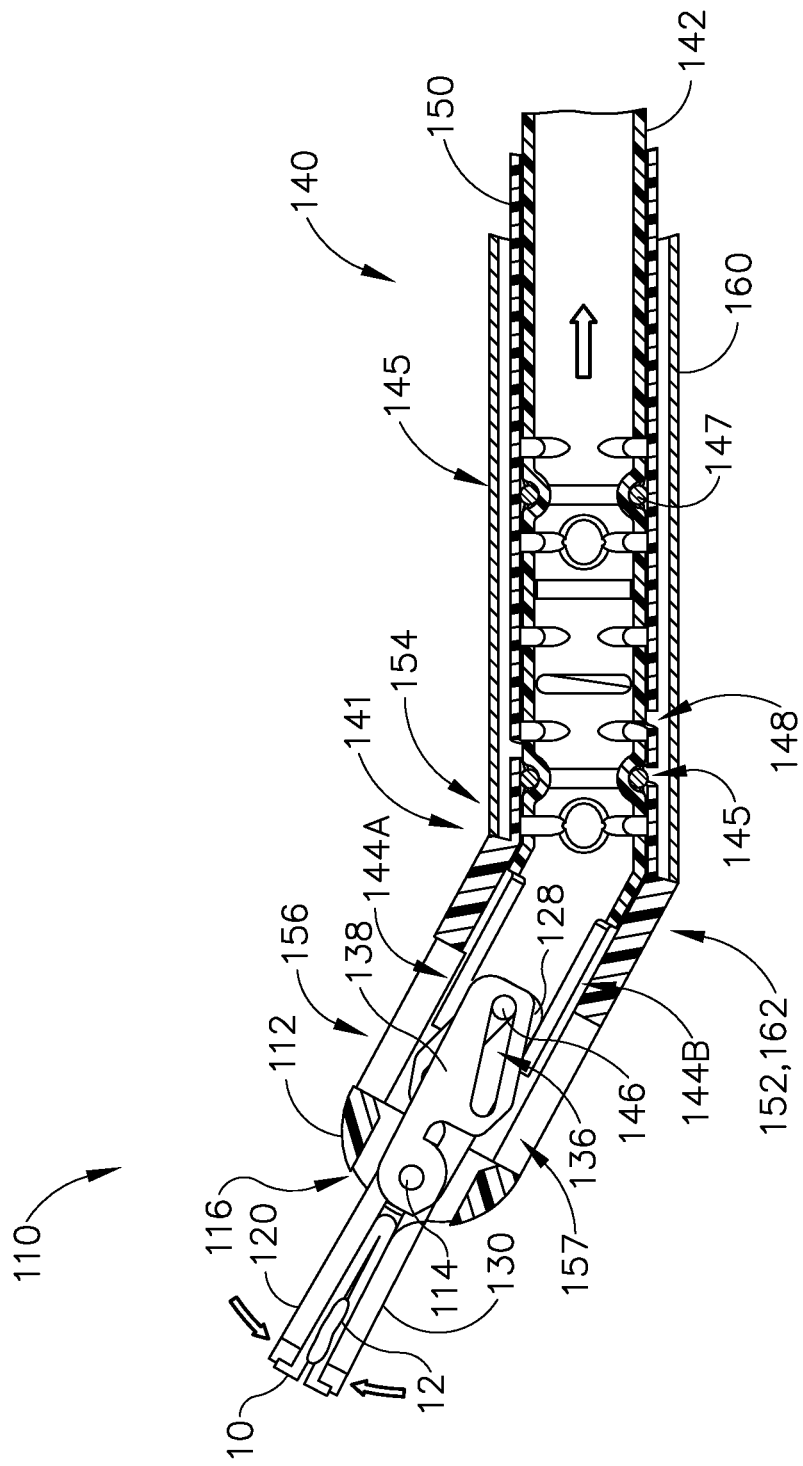
FIG. 12B depicts a cross-sectional view of the end effector of FIG. 5 in an articulated position, taken along line 12-12 of FIG. 11, with the pair of jaws in a closed position about the blood vessel.

Articulation knob (172) is secured to a proximal portion of middle articulation tube (150). Articulation knob (172) is operable to rotate middle articulation tube (150) relative to handle assembly (170). Push/pull tube (142) is configured such that push/pull tube (142) rotates with middle articulation tube (150). A proximal end of outer ground tube (160) is secured to body (178) of handle assembly (170) such that outer ground tube (160) does not rotate relative to handle assembly (170). It should therefore be understood that as articulation knob (172) rotates middle articulation tube (150), outer ground tube (160) remains stationary. Thus, as middle articulation tube (150) rotates, the relationship between first sloped face (152) and second sloped face (162) changes and causes articulation of the distal portion of middle articulation tube (150) as shown in FIG. 11. As middle articulation tube (150) is articulated, it should be appreciated that push/pull tube (142) will articulate as well. As shown in FIGS. 12A-12B, in this articulated position, push/pull tube (142) remains translatable within shaft assembly (140); and thus jaws (120, 130) may be driven to the closed position when shaft assembly (140) is in an articulated state.

Figure 13:
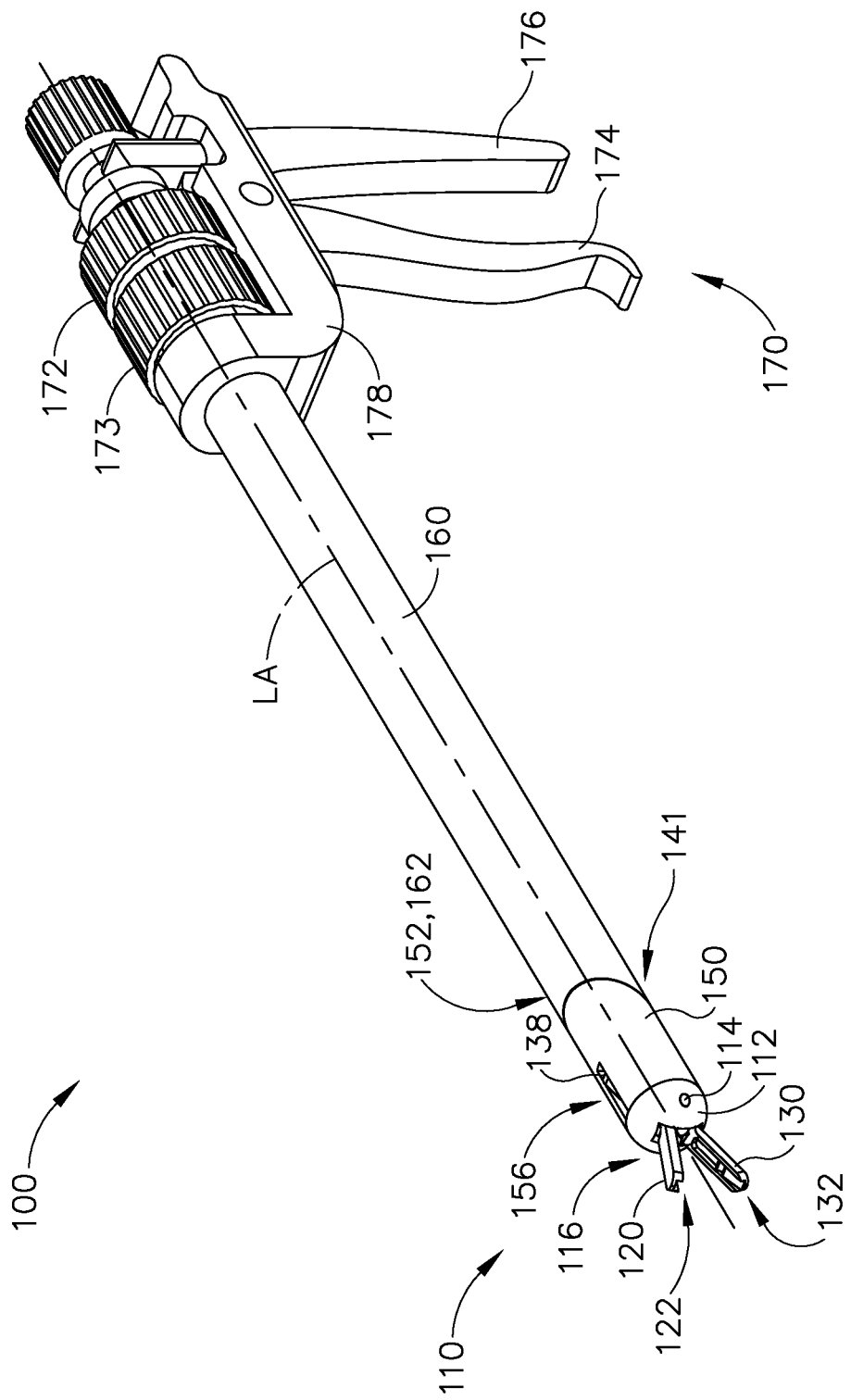
FIG. 13 depicts a perspective view of an exemplary alternative clip applier instrument

As shown in FIG. 13, some versions of instrument (100) may further comprise a rotation knob (173) secured to a proximal end of outer ground tube (160). Rotation knob (173) is configured to cause outer ground tube (160) to rotate relative to handle assembly (170). Rotation knob (173) may be configured such that rotation of rotation knob (173) causes concurrent rotation of articulation knob (172) such that outer ground tube (160), middle articulation tube (150), and push/pull tube (142) rotate together relative to handle assembly (170). It should therefore be appreciated that rotation of rotation knob (173) would cause shaft assembly (140) to rotate without articulating middle articulation tube (150) and/or push/pull tube (142). Rotation knob (173) may be further configured such that rotation of articulation knob (172) will not cause rotation of rotation knob (173). It should therefore be understood shaft assembly (140) may be rotated and middle articulation tube (150) and push/pull tube (142) may be articulated to achieve a multitude of positions and orientations. It should also be understood that rotation knob (173) may rotate push/pull tube (142), middle articulation tube (150), and outer ground tube (160) relative to handle assembly (170) regardless of whether articulation joint (141) is in an articulated or non-articulated state.

It should be understood that, among other components, wires, tubes, or electrode elements may be disposed within the interior of push/pull tube (142). Such wires, tubes, or electrode elements may provide, among other things, energy or fluids to end effector (110) and/or jaws (120, 130).

IV. Miscellaneous

While shaft assembly (140) is described herein as being incorporated into a clip applier (100), shaft assembly (140) may instead be readily incorporated into various other kinds of medical instruments (e.g. surgical staplers, tissue graspers, surgical cutters, ultrasonic devices, electrosurgical devices, etc.). Merely illustrative examples of stapling instruments in which shaft assembly (140) may be readily incorporated are disclosed in U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; and U.S. Pat. No. 7,404,508, entitled "Surgical Stapling and Cutting Device," issued Jul. 29, 2008. The disclosure of each of the above-cited U.S. patents is incorporated by reference herein.

Merely illustrative examples of electrosurgical instruments in which shaft assembly (140) may be readily incorporated are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein. Other kinds of electrosurgical instruments that may incorporate shaft assembly (140) and variations thereof will be apparent to those of ordinary skill in the art in view of the teachings herein.

Merely illustrative examples of ultrasonic surgical instruments in which shaft assembly (140) may be readily incorporated are disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other kinds of ultrasonic surgical instruments that may incorporate shaft assembly (140) and variations thereof will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An instrument, wherein the instrument comprises:
   (a) a body comprising a trigger and an articulation control member;
   (b) a shaft assembly extending distally from the body, wherein the shaft assembly comprises:
      (i) an outer tube coupled to the body, wherein a distal end of the outer tube presents a first angled face,
      (ii) a middle articulation tube rotatably disposed within the outer tube and coupled to the articulation control member, wherein a distal portion of the middle articulation tube presents a second angled face matingly engaged with the first angled face, wherein the articulation control member is configured to rotate to thereby cause rotation of the middle articulation tube, wherein the middle articulation tube is configured to rotate to thereby cause articulation of the distal portion of the middle articulation tube through engagement between the first angled face and the second angled face, and
      (iii) a push/pull tube slidably disposed within the middle articulation tube, wherein the middle articulation tube is configured to articulate the push/pull tube, wherein the trigger is configured to actuate to thereby cause longitudinal translation of the push/pull tube relative to the body; and
   (c) an end effector disposed at a distal end of the middle articulation tube, wherein the end effector comprises a pair of jaws, wherein the push/pull tube is configured to longitudinally translate to thereby drive the pair of jaws into a closed position.

2. The instrument of claim 1, wherein the body comprises a handle assembly having a pistol grip, and wherein the trigger is operable to pivot toward and away from the pistol grip.

3. The instrument of claim 1, further comprising a rack and pinion assembly coupling the trigger with the push/pull tube.

4. The instrument of claim 1, wherein the first angled face and the second angle face are respectively defined by a first plane and a second plane, and wherein the first plane and the second plane are defined by angles oblique to a longitudinal axis defined by the shaft assembly.

5. The instrument of claim 4, wherein the oblique angles of the first plane and the second plane are equal.

6. The instrument of claim 4, wherein the oblique angles are oriented in opposite directions.

7. The instrument of claim 1, wherein the end effector further comprises a round cap secured to a distal end of the middle articulation tube, wherein the jaws are pivotably disposed within a slot defined within the round cap.

8. The instrument of claim 1, wherein a proximal portion of each jaw of the pair of jaws comprises a slot.

9. The instrument of claim 8, wherein the push/pull tube comprises a drive pin located at a distal end of the push/pull tube.

10. The instrument of claim 9, wherein the drive pin is slidably disposed within each slot of the pair of jaws.

11. The instrument of claim 10, wherein each slot is substantially straight.

12. The instrument of claim 1, wherein a distal portion of each jaw of the pair of jaws comprises a channel configured to receive and removably secure a surgical clip.

13. The instrument of claim 1, wherein the push/pull tube comprises a plurality of articulation slots configured to provide flexibility.

14. The instrument of claim 1, wherein the push/pull tube comprises a plurality of ball bearing detents and a plurality of ball bearings positioned in the bearing detents.

15. The instrument of claim 14, wherein the ball bearings are configured to bear upon an interior surface of the middle articulation tube.

16. The instrument of claim 1, wherein the middle articulation tube comprises an articulation feature configured to provide flexibility.

17. The instrument of claim 1, wherein the body further comprises a rotation member secured to the outer tube, wherein the rotation member is configured to rotate to thereby cause rotation of the outer tube.

18. The instrument of claim 17, wherein the rotation member is further configured to rotate to thereby cause rotation of the shaft assembly and end effector.

19. An instrument, wherein the instrument comprises:
    (a) a handle assembly, comprising:
        (i) a pistol grip, and
        (ii) a trigger pivotable toward and away from the pistol grip;
    (b) a shaft assembly extending distally from the handle assembly, wherein the shaft assembly comprises:
        (i) an outer tube coupled to the handle assembly, wherein a distal end of the outer tube presents a first angled face defined by a first plane at a first angle oblique to a longitudinal axis defined by the shaft assembly,
        (ii) a middle articulation tube rotatably disposed within the outer tube, wherein the middle articulation tube comprises a first articulation feature configured to provide flexibility, wherein a distal portion of the middle articulation tube presents a second angled face defined by a second plane at a second angle oblique to the longitudinal axis, wherein the first angled face and the second angled face are in contact, wherein the middle articulation tube is configured to rotate to cause articulation of the distal portion of the middle articulation tube, and
        (iii) a push/pull tube slidably disposed within the middle articulation tube, wherein the push/pull tube comprises a second articulation feature configured to provide flexibility, wherein the first angled face and the second angle face are in contact proximal to the first and second articulation features, wherein the middle articulation tube is configured to articulate to cause articulation of the push/pull tube, wherein the pivoting trigger is configured to pivot to cause longitudinal translation of the push/pull tube relative to the handle assembly; and
    (c) an end effector disposed at a distal end of the middle articulation tube, wherein the end effector comprises a pair of jaws, wherein the push/pull tube is configured to longitudinally translate to drive the pair of jaws into a closed position.

20. An instrument for clamping a surgical clip, wherein the instrument comprises:
    (a) a handle assembly comprising a trigger and an articulation member;
    (b) a shaft assembly extending distally from the handle assembly, wherein the shaft assembly comprises:
        (i) an outer tube coupled to the handle assembly, wherein a distal end of the outer tube presents a first angled face,
        (ii) a middle articulation tube rotatably disposed within the outer tube and coupled to the articulation member, wherein a distal portion of the middle articulation tube presents a second angled face matingly engaged with the first angled face, wherein the articulation member is configured to rotate to cause rotation of the middle articulation tube, wherein the middle articulation tube is configured to rotate to cause articulation of the distal portion of the middle articulation tube, and
        (iii) a push/pull tube slidably disposed within the middle articulation tube, wherein the middle articulation tube is configured to articulate to cause articulation of the push/pull tube, wherein the push/pull tube comprises a drive pin located at a distal end of the push/pull tube, wherein the trigger is configured to actuate to cause longitudinal translation of the push/pull tube relative to the handle assembly; and
    (c) an end effector disposed at a distal end of the middle articulation tube, wherein the end effector comprises a pair of jaws, wherein a proximal portion of each jaw of the pair of jaws comprises a slot, wherein the drive pin of the push/pull tube is slidably disposed within each slot of the pair of jaws, wherein a distal portion of each jaw of the pair of jaws comprises a channel configured to receive a surgical clip, wherein the jaws are configured to pivot about a point between the respective slot and the respective channel, wherein to push/pull tube is configured to longitudinally translate to cause the pair of jaws to pivot.

* * * * *